US011066630B2

(12) United States Patent
Kilic et al.

(10) Patent No.: US 11,066,630 B2
(45) Date of Patent: Jul. 20, 2021

(54) DEVICE AND METHOD FOR ANALYSIS OF TISSUE CONSTRUCTS

(71) Applicant: The Johns Hopkins University, Baltimore, MD (US)

(72) Inventors: Onur Kilic, Baltimore, MD (US); Steven An, Baltimore, MD (US); Andre Levchenko, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 412 days.

(21) Appl. No.: 15/739,639

(22) PCT Filed: Jul. 1, 2016

(86) PCT No.: PCT/US2016/040695
§ 371 (c)(1),
(2) Date: Dec. 22, 2017

(87) PCT Pub. No.: WO2017/004516
PCT Pub. Date: Jan. 5, 2017

(65) Prior Publication Data
US 2018/0171276 A1    Jun. 21, 2018

Related U.S. Application Data

(60) Provisional application No. 62/187,641, filed on Jul. 1, 2015.

(51) Int. Cl.
*C12N 5/07* (2010.01)
*C12N 5/073* (2010.01)
*C12N 5/074* (2010.01)
*C12M 1/12* (2006.01)
*C12M 3/06* (2006.01)
*C12M 3/00* (2006.01)

(52) U.S. Cl.
CPC ............ *C12M 21/08* (2013.01); *C12M 23/16* (2013.01); *C12M 25/02* (2013.01); *C12N 5/0696* (2013.01)

(58) Field of Classification Search
None
See application file for complete search history.

(56) References Cited

U.S. PATENT DOCUMENTS

| | | | | |
|---|---|---|---|---|
| 5,486,457 | A * | 1/1996 | Butler | C12M 35/06 435/7.2 |
| 8,288,159 | B2 | 10/2012 | Warren et al. | |
| 2004/0147015 | A1* | 7/2004 | El-Haj | C12M 35/04 435/325 |
| 2011/0171689 | A1 | 7/2011 | Warren et al. | |
| 2011/0250585 | A1* | 10/2011 | Ingber | C12N 5/061 435/5 |
| 2012/0214191 | A1* | 8/2012 | Barker | G01N 1/312 435/29 |
| 2014/0038279 | A1* | 2/2014 | Ingber | C12M 25/02 435/297.2 |
| 2014/0093906 | A1 | 4/2014 | Ingber | |
| 2014/0335496 | A1 | 11/2014 | Grego et al. | |
| 2015/0004692 | A1* | 1/2015 | Le Berre | B29C 39/42 435/366 |

* cited by examiner

*Primary Examiner* — Jill A Warden
*Assistant Examiner* — Brittany I Fisher
(74) *Attorney, Agent, or Firm* — DLA Piper LLP (US)

(57) ABSTRACT

The present invention provides an integrated microphysiological device and fabrication methods thereof, as well as methods of use to perform biological assays.

43 Claims, 25 Drawing Sheets

After brain layer formation, endothelial cells are introduced into the vascular layer of the chip Endothelial barrier strength is monitored using TEER through the chip access holes

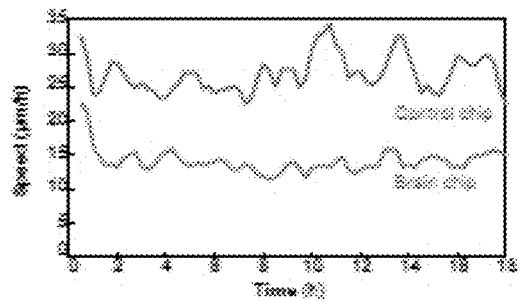
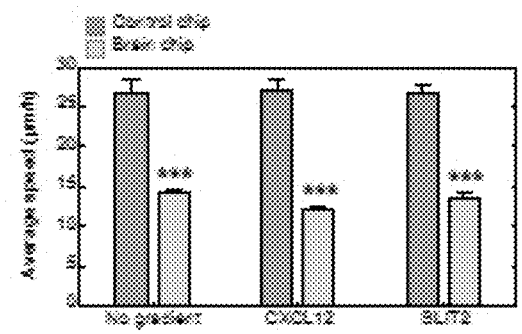
FIG. 11A  FIG. 11B
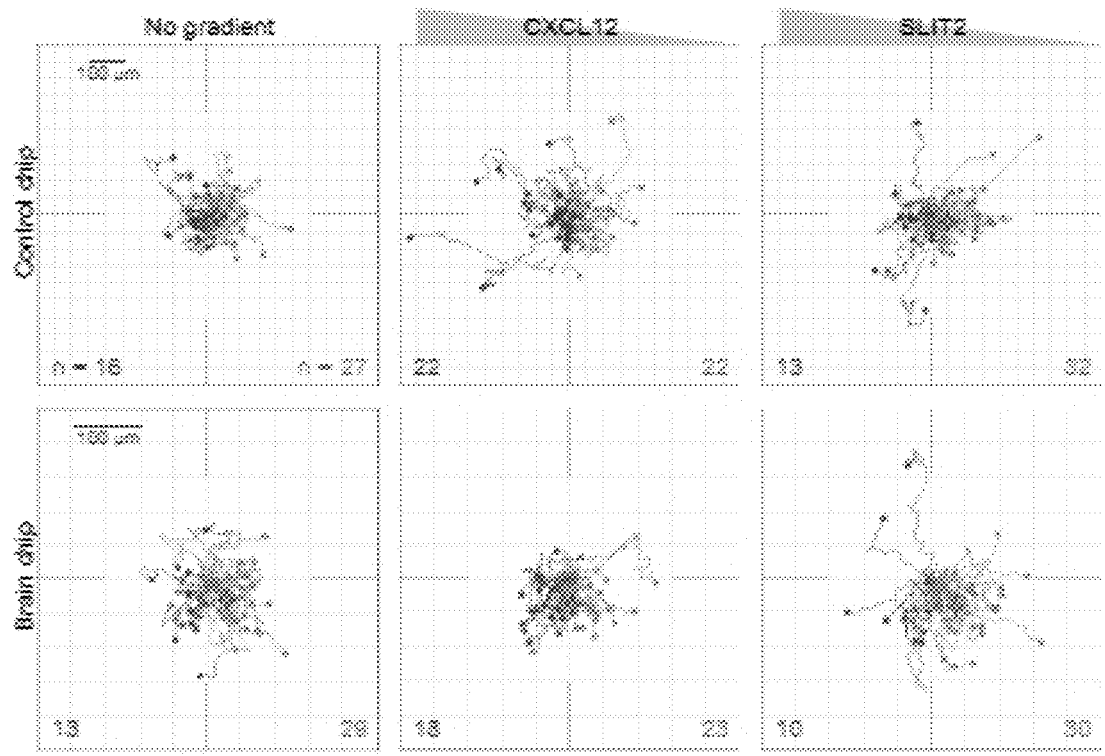
FIG. 11C

DEVICE AND METHOD FOR ANALYSIS OF TISSUE CONSTRUCTS

CROSS-REFERENCE TO RELATED APPLICATIONS

This application is a 35 USC § 371 National Stage application of International Application No. PCT/US2016/0040695 filed Jul. 1, 2016, which claims the benefit under 35 USC § 119(e) to U.S. Application Ser. No. 62/187,641 filed Jul. 1, 2015. The disclosure of each of the prior applications is considered part of and is incorporated by reference in the disclosure of this application.

BACKGROUND OF THE INVENTION

Field of the Invention

The invention relates generally to integrated microphysiological systems and more specifically to an integrated microphysiological device as well as methods of use thereof to perform biological assays.

BACKGROUND INFORMATION

Animal studies are costly, and typically long and controversial. Of even greater concerns are validity problems in cross-species extrapolation. Although physiologically more relevant than in-vitro models, animal studies allow limited control of individual variables. As such, it is often difficult to extract specific information from the experiments. On the other hand, standard in-vitro models such as cell culture and microfluidic experiments are usually too simplistic in design. Therefore, there is a need for 'bridging the gap' between in-vivo and in-vitro studies through a more representative cellular environment. One method is employing 3D cell cultures, or organ-chips, that reconstitute various functionalities of human organs. These platforms allow extensive control on the cellular microenvironment while recapitulating important physiologic conditions. Although these microphysiological systems are still at their infancy, they have tremendous potential to transform basic biomedical research and drug discovery, since they can serve as a first step before clinical trials.

As such, there exists a need for more advanced platforms to perform meaningful biomedical research. The tools described herein, allow long-term cell growth using standard culturing techniques, and can be readily adopted for various biomedical research purposes. Importantly, they are user friendly and do not require technical expertise in microfluidics. Such platforms may be used to study the mechanisms and new treatments for human diseases, such as asthma and brain cancer.

SUMMARY OF THE INVENTION

The invention provides a chip platform that mimics important aspects of human tissues or organs, and is easy to manufacture and convenient to use. The platform allows faster drug or treatment development for human diseases, such as airway related conditions, and makes the initial testing on drugs and compounds safer, as it does not involve human subjects.

Accordingly, in one aspect, the present invention provides a microphysiology device for mimicking characteristics of a biological tissue. The device includes a body having a top compartment and a bottom compartment separated by a porous membrane that is at least partially optically transparent. The membrane is coated with at least one attachment molecule that supports the attachment of a plurality of living cells. In embodiments, the device further includes at least two access ports through the body. The first port provides a fluid path through the body into the top compartment, and the second port provides a fluid path through the body into the bottom compartment. Further, a pressure applied to the top compartment through one or more of the ports introduces a compressive stress gradient on the cells attached to the membrane. In embodiments, the device further comprises a source of electromagnetic radiation for providing an electromagnetic field to cells cultured in the device and optionally an imaging component for monitoring cell behavior and movement.

In another aspect, the present invention provides a method of fabricating a microphysiology device of the disclosure. The method includes attaching a polydimethylsiloxane structure to a polycarbonate or polyester membrane. Attachment includes exposing the polydimethylsiloxane structure and the membrane to an oxygen plasma to chemically activate their surfaces; wetting the surface of the polydimethylsiloxane structure, the membrane, or combination thereof, with a bonding solution of 1% (3-aminopropyl) triethoxysilane in water after plasma treatment; and contacting the polydimethylsiloxane structure with the membrane to cause permanent bonding upon evaporation of the water in the bonding solution.

In yet another aspect, the present invention provides a method for performing a biological assay using the microphysiology device of the disclosure. The method includes providing a device of the disclosure, wherein at least one side of the membrane and the bottom compartment are coated with living cells; applying a magnetic field in the horizontal direction to magnetize the magnetic beads attached to the cells in the bottom compartment; and monitoring behavior of cells in the bottom compartment by applying a magnetic field oscillating in the vertical direction that forces the magnetic beads into a twisting motion. In embodiments the horizontal component of the twisting motion is recorded using a microscope imaging the magnetic beads.

In still another aspect, the present invention provides a method for determining an effect of at least one stimulus on cells within the microphysiology device of the disclosure. The method includes applying a stimulus to the top compartment, bottom compartment, or both, wherein the stimulus is physical, chemical, or biological in nature; and monitoring behavior of cells in the bottom compartment. In embodiments, monitoring includes assaying secretion and biochemical activity profiles, microrheological characteristics, or mechanical properties of the cells.

BRIEF DESCRIPTION OF THE DRAWINGS

FIG. 9A is a schematic illustrating addition of cells to a microphysiology device. FIG. 9B is a schematic illustrating growth and differentiation of cells in the microphysiology device. FIG. 9C is a schematic illustrating addition of additional cell types to existing differentiated cells in the microphysiology device. FIG. 9D is a schematic illustrating monitoring of activity in the microphysiology device using TEER. FIG. 9E is a graph depicting TEER data of cells within a microphysiology device.

FIG. 10A is a schematic illustrating addition of cells to a microphysiology device. FIG. 10B is a schematic illustrating stimulation or inhibition of cells in the microphysiology device. FIG. 10C depict varying CXCL12 expression in cells after application of a chemical gradient in the device. FIG. 10D depict varying CXCL12 expression in cells after application of a chemical gradient in the device. FIG. 10E depict varying SLIT2 expression in cells after application of a chemical gradient in the device. FIG. 10F depict varying SLIT2 expression in cells after application of a chemical gradient in the device.

FIGS. 11A-11F are a series of graphical representations of experimental data generated using a microphysiology device for modeling the brain compared to control. FIG. 11A is a graph depicting data using the device. FIG. 11B is a histogram depicting data using the device. FIG. 11C is a series of graphs comparing gene expression using the device. FIG. 11D is a series of graphs comparing gene expression using the device. FIG. 11E is a graph depicting data using the device. FIG. 11F is a graph depicting data using the device.

FIG. 12A is a schematic illustrating signaling in airway epithelium. FIG. 12B is a schematic illustrating a microphysiology device for modeling lung tissue. FIG. 12C is an image of a smooth-muscle layer grown in the device. FIG. 12D depicts data using the device.

FIG. 13A is a schematic illustrating a microphysiology device for modeling lung tissue. FIG. 13B depicts data using the device. FIG. 13C depicts data using the device. FIG. 13D depicts data using the device.

FIG. 14A depicts data relating to COX1 and COX2 expression. FIG. 14B depicts data regarding $PGE_2$ content.

FIG. 15A is a graph depicting data. FIG. 15B is a graph depicting data. FIG. 15C is a graph depicting data. FIG. 15D is a graph depicting data. FIG. 15E is an image of a gel depicting gene expression.

FIG. 16A is a graph depicting data. FIG. 16B is a graph depicting data. FIG. 16C is a graph depicting data. FIG. 16D is a graph depicting data. FIG. 16E is a graph depicting data. FIG. 16F is a graph depicting data. FIG. 16G is an image of a gel depicting gene expression. FIG. 16H is a graph depicting data.

FIG. 17A is a schematic illustrating an airway feedback model. FIG. 17B is a series of graphs regarding predictions of an ODE model. FIG. 17C depicts data relating to compressive stress. FIG. 17D depicts data relating to compressive stress.

FIG. 18A is a schematic illustrating components of the device. FIG. 18B is a schematic illustrating components of the device. FIG. 18C is an image illustrating cells of the device. FIG. 18D is a schematic illustrating the device. FIG. 18E is a schematic illustrating components of the device.

FIG. 19A is a graph depicting data. FIG. 19B is a graph depicting data. FIG. 19C is a graph depicting data. FIG. 19D is a graph depicting data.

FIG. 20A is a graph depicting data. FIG. 20B is a graph depicting data. FIG. 20C is a graph depicting data.

FIG. 21A is a graph depicting data. FIG. 21B is a table depicting data.

DETAILED DESCRIPTION OF THE INVENTION

The invention provides an organ or tissue mimicking platform that is convenient to use and manufacture, whereby two or more types of cells can interact through one or more porous membranes, that can be inflexible or flexible. The platform allows application of physical, chemical, or biological stimuli on the cells and assaying their secretion and biochemical activity profiles, their microrheological characteristics, or their mechanical properties. The device combines long term cell cultures mimicking the arrangement of the cells in actual tissue with biological, microrheological, or mechanical studies, and allows an easy-to-use platform that does not require significant training to use.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The device platform of the present disclosure is convenient and easy to use, which is extremely important in laboratory settings and increases the chance of wider adoption and use substantially. Furthermore, an innovative manufacturing technique is disclosure that makes it much easier and cheaper to construct a device of the disclosure in comparison to other devices that provide tissue or organ mimicking capabilities.

Figure 1:
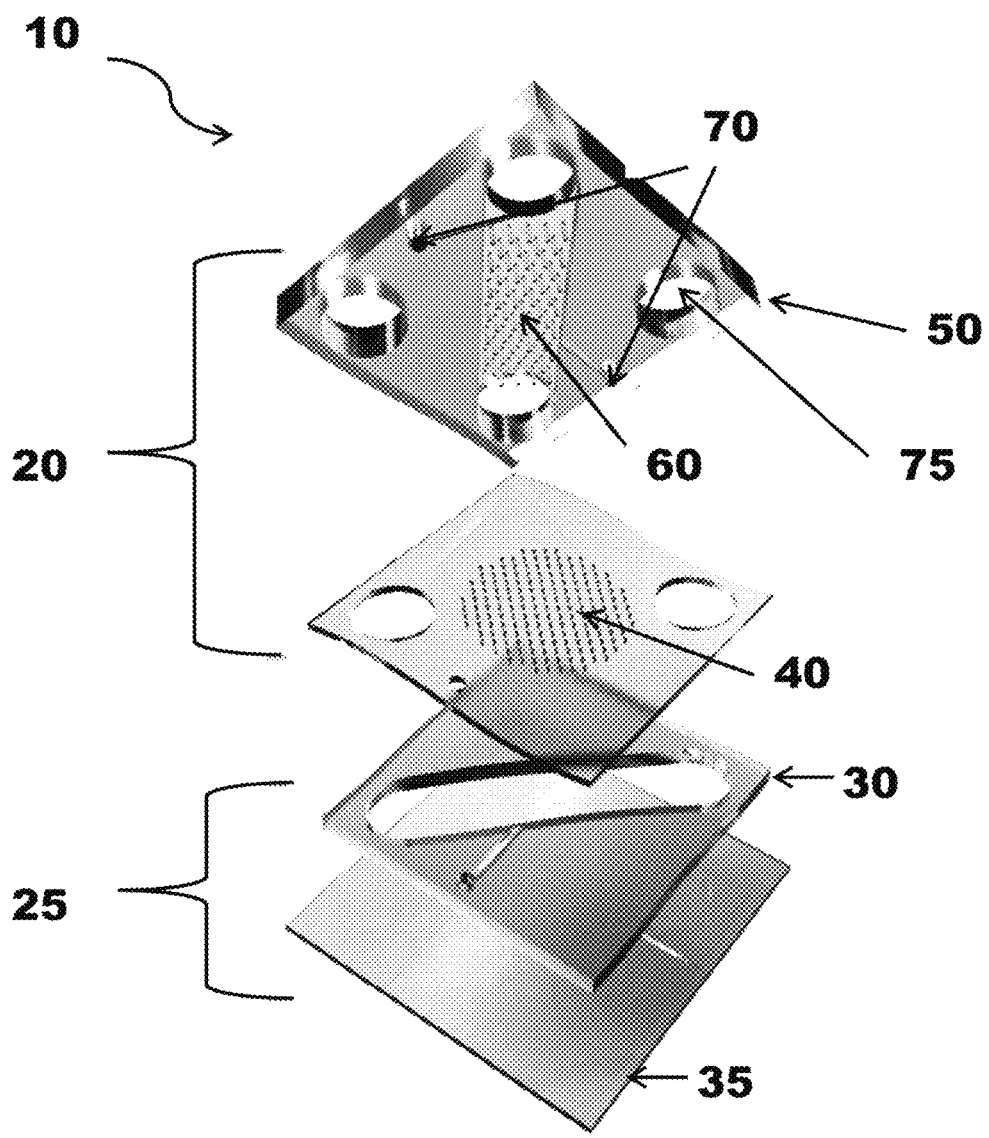
FIG. 1 is an exploded schematic of a microphysiology device 10 according to one embodiment of the invention.
Figure 2:
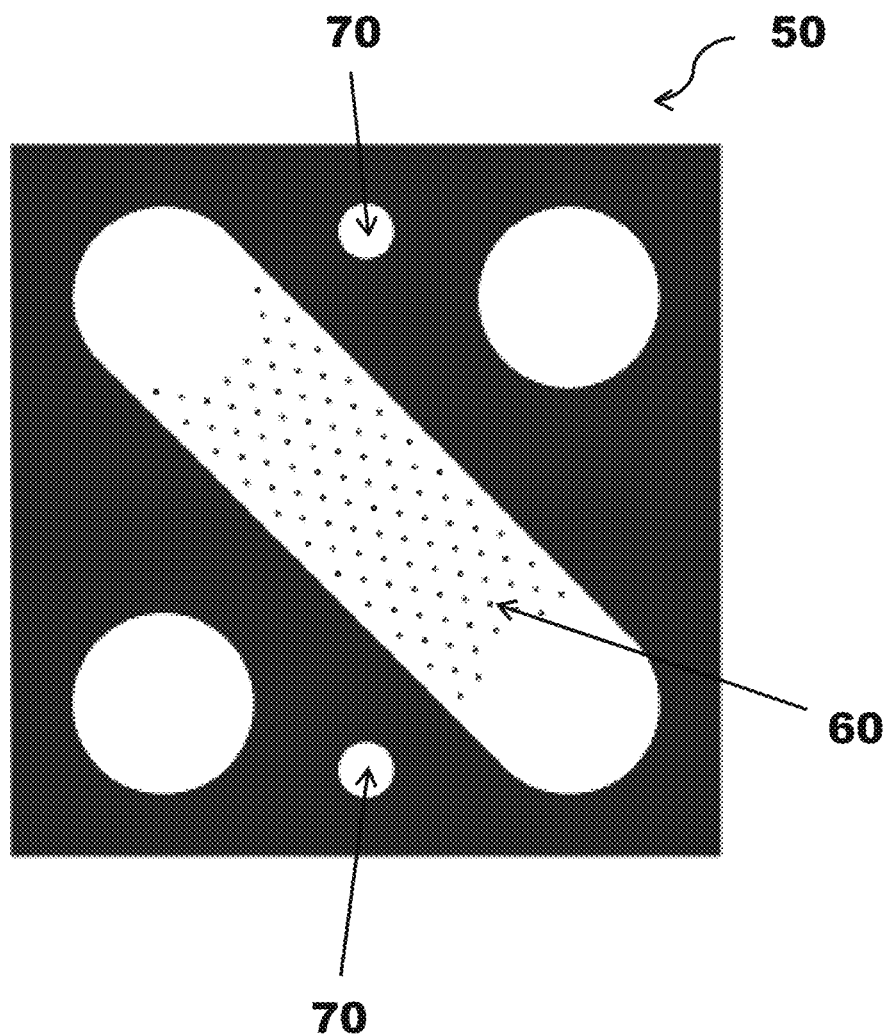
FIG. 2 is a top view of upper plate 50 according to one embodiment of the invention.

Accordingly, in one aspect, the present invention provides a microphysiology device 10 for mimicking a biological tissue. With reference to FIG. 1, the device 10 includes a body having a top compartment 20 and a bottom compartment 25 separated by a porous membrane 40. Membrane 40 may be partially or entirely optically transparent to allow visual inspection of cells being cultured within the device.

Figure 5:
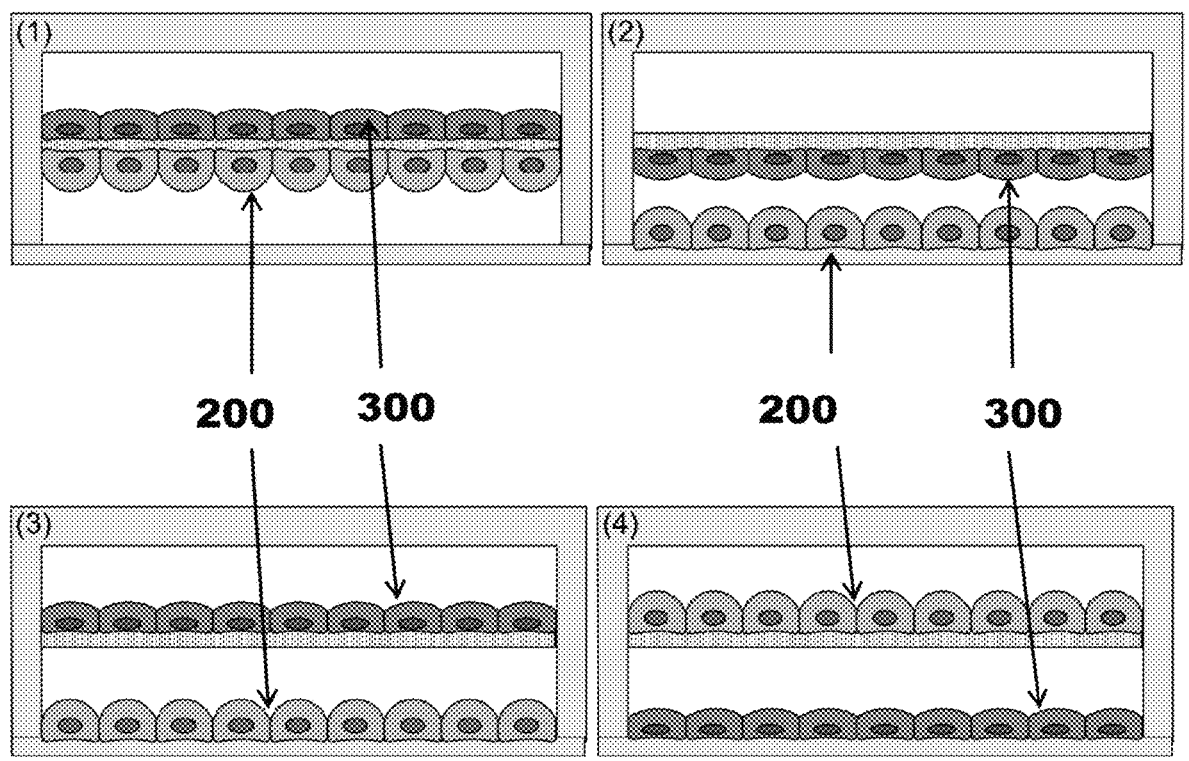
FIG. 5 is a series of schematic representations depicting different apical-basal interactions which are possible between two cell types (200 and 300).
Figure 6:
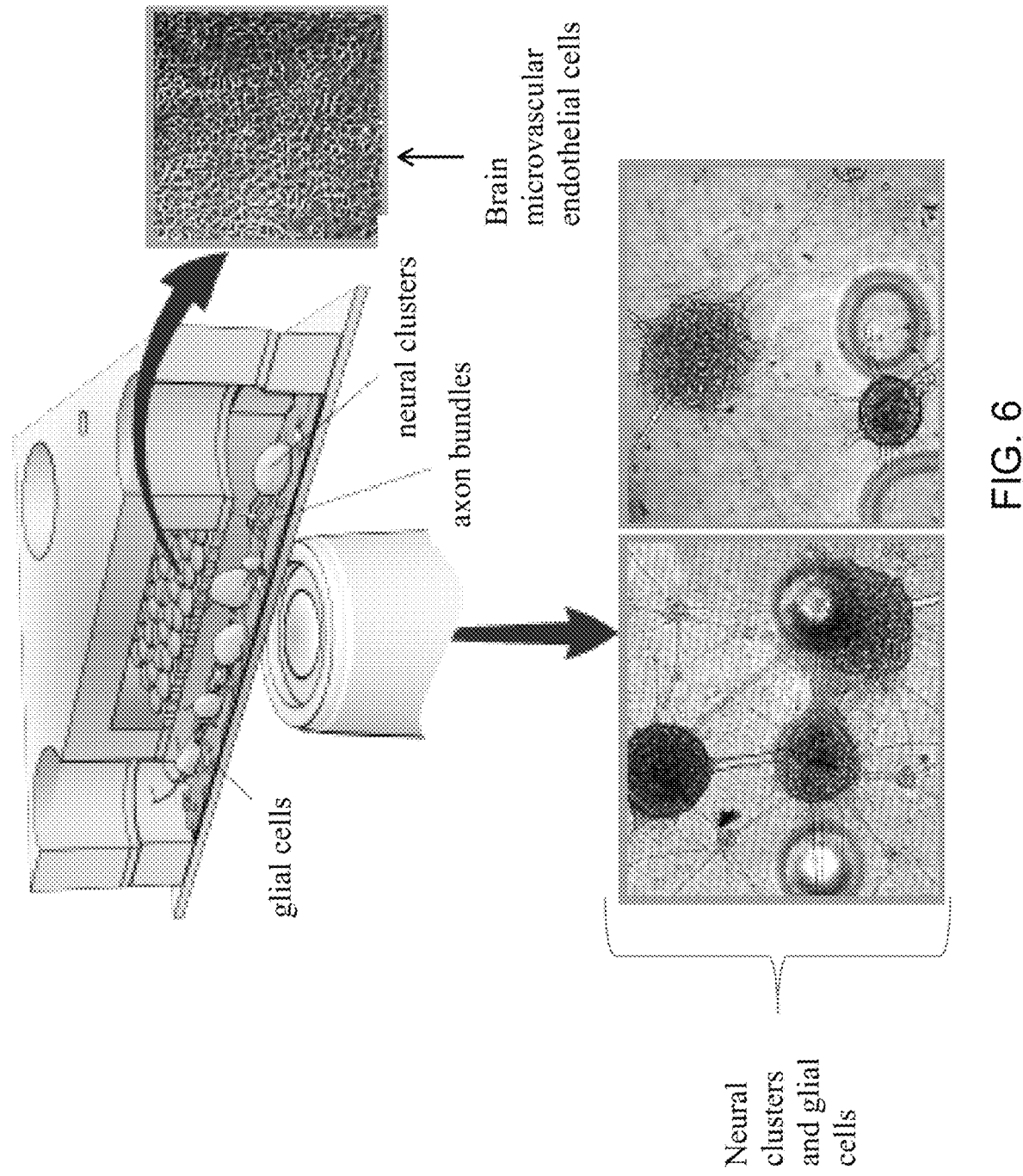
FIG. 6 is a series of schematic and pictorial representations depicting use of a microphysiology device according to one embodiment of the invention for modeling brain tissue.
Figure 7:
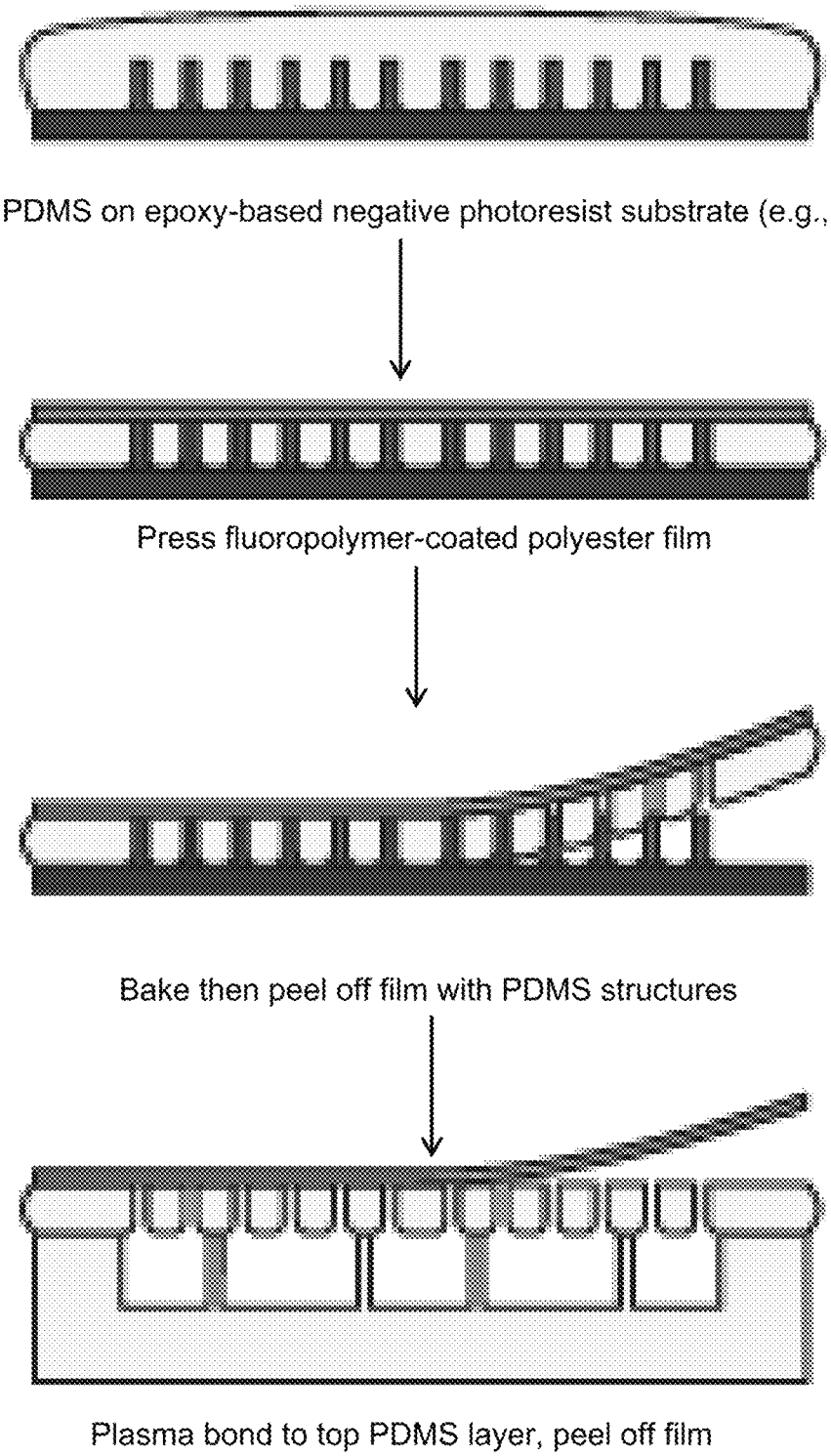
FIG. 7 is a schematic flow chart illustrating manufacture of a microphysiology device according to one embodiment of the invention for modeling vascular tissue.
Figure 8:
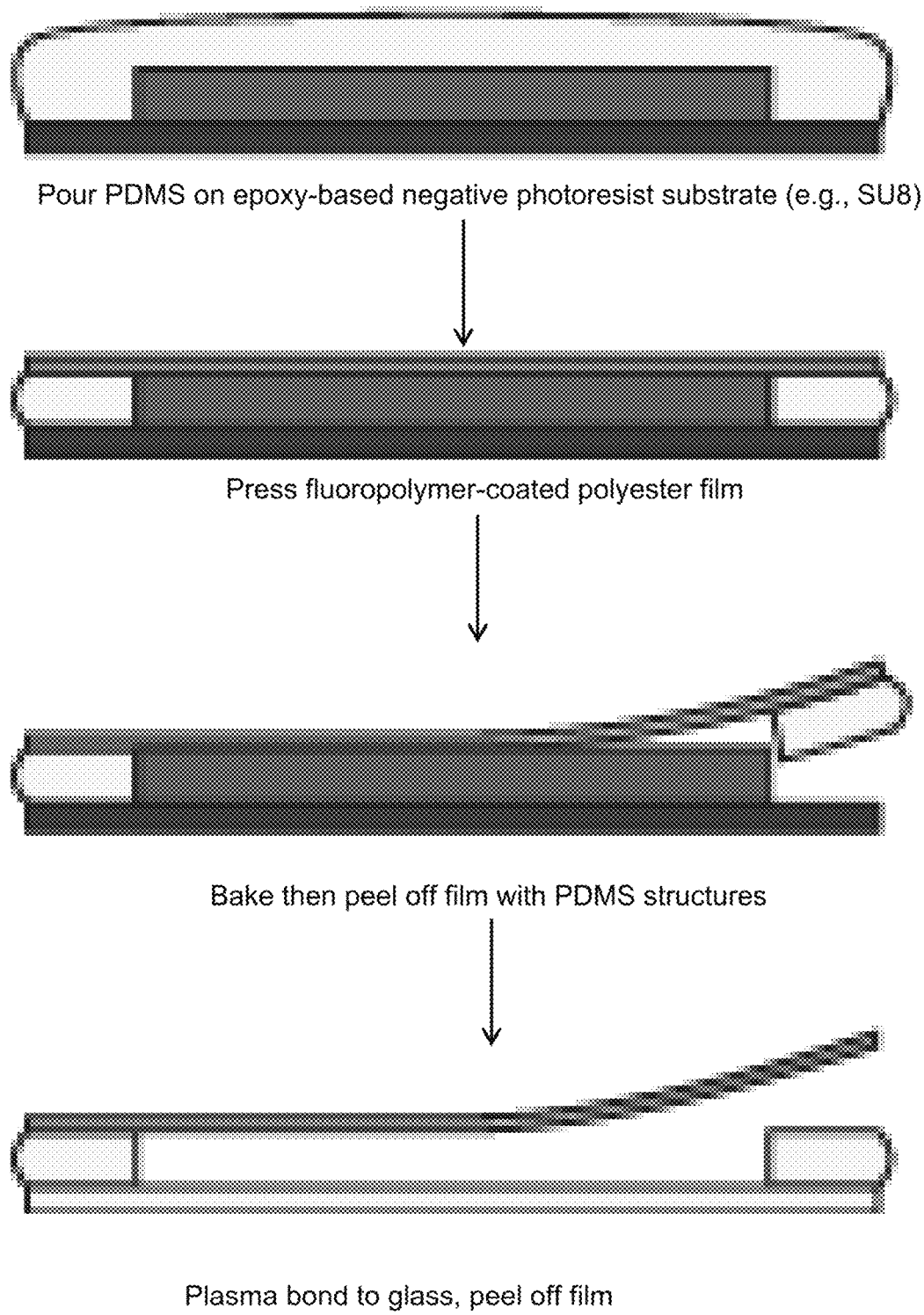
FIG. 8 is a schematic flow chart illustrating manufacture of a microphysiology device according to one embodiment of the invention for modeling brain tissue.
Figure 9A:
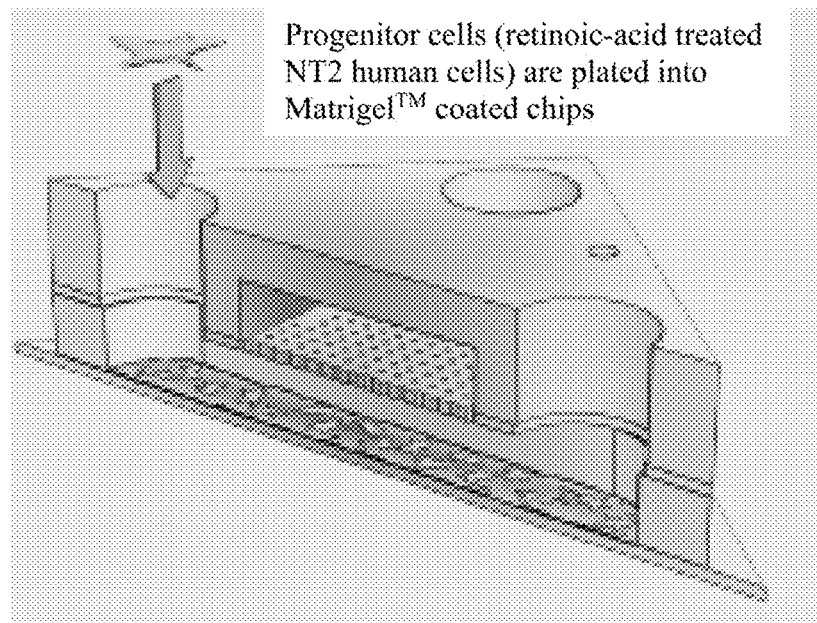
FIGS. 9A-9E are a series of schematic and graphical representations of a microphysiology device for modeling the brain in embodiments of the invention as well as experimental data generated using the device.
Figure 9B:
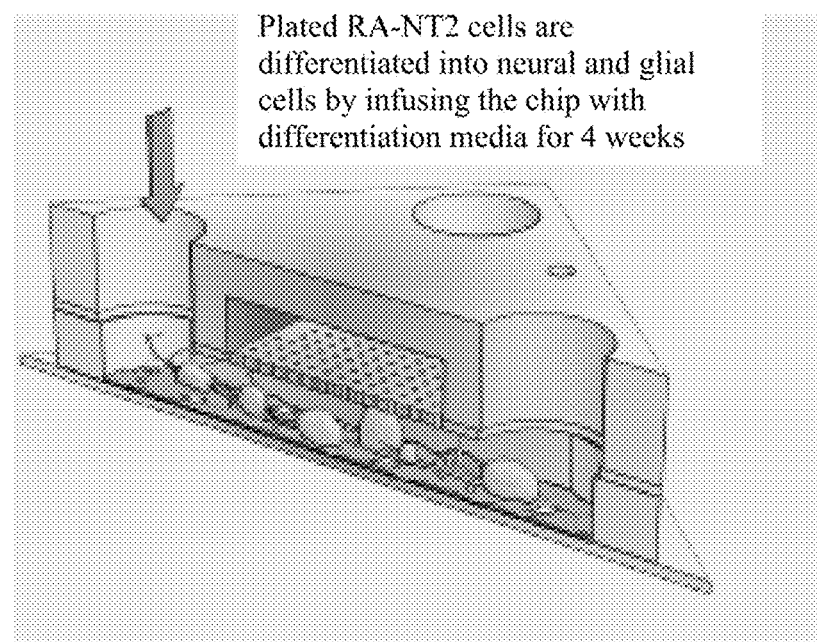
Figure 9C:
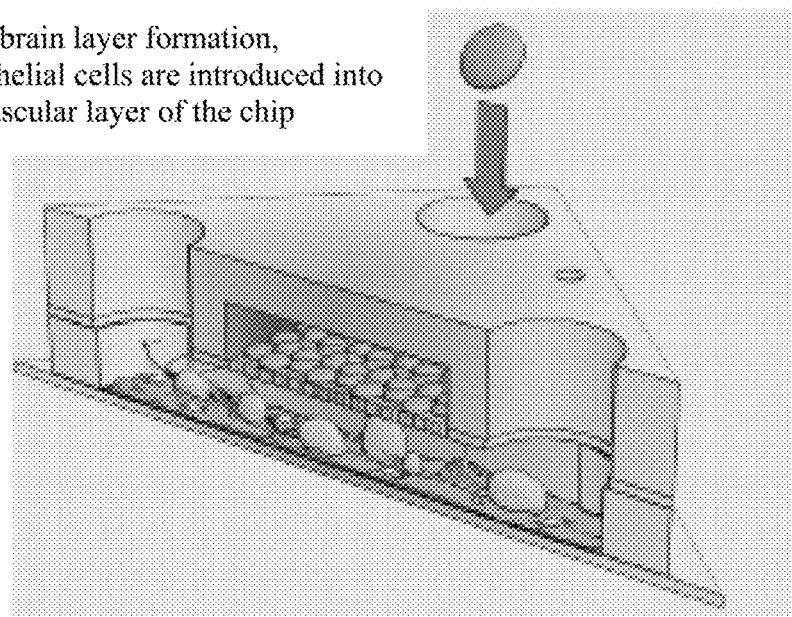
Figure 9D:
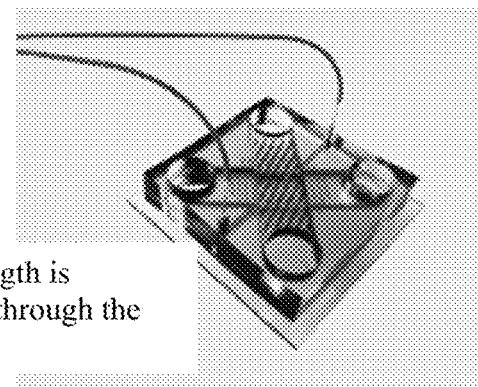
Figure 9E:
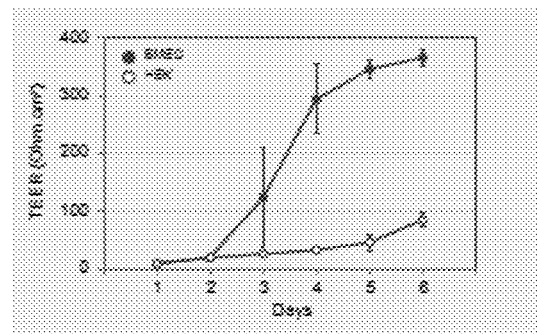
Figure 10A:
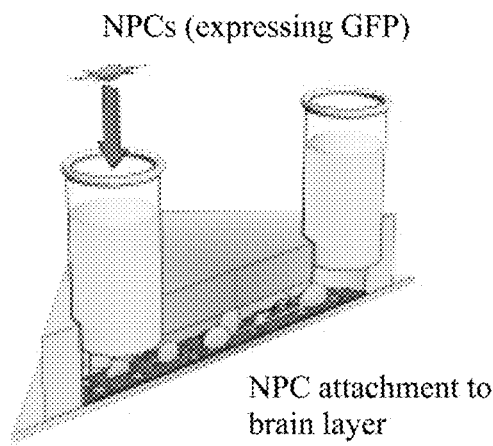
FIGS. 10A-10F are a series of schematic and graphical representations of a microphysiology device for modeling the brain in embodiments of the invention as well as experimental data generated using the device.
Figure 10B:
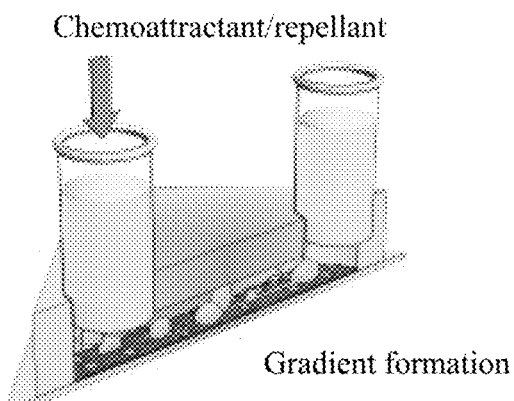
Figure 10C:
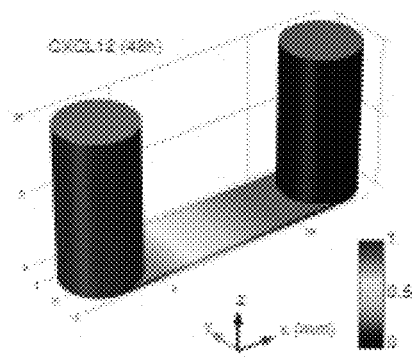
Figure 10D:
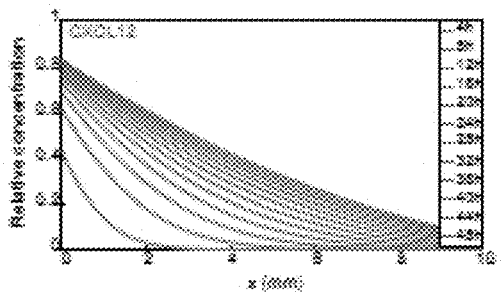
Figure 10E:
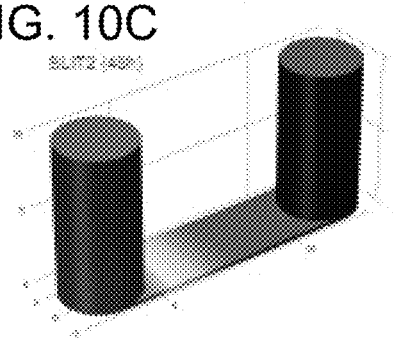
Figure 10F:
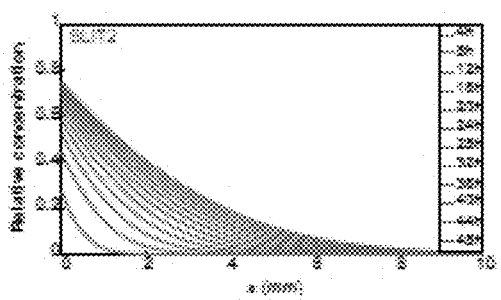
Figure 11D:
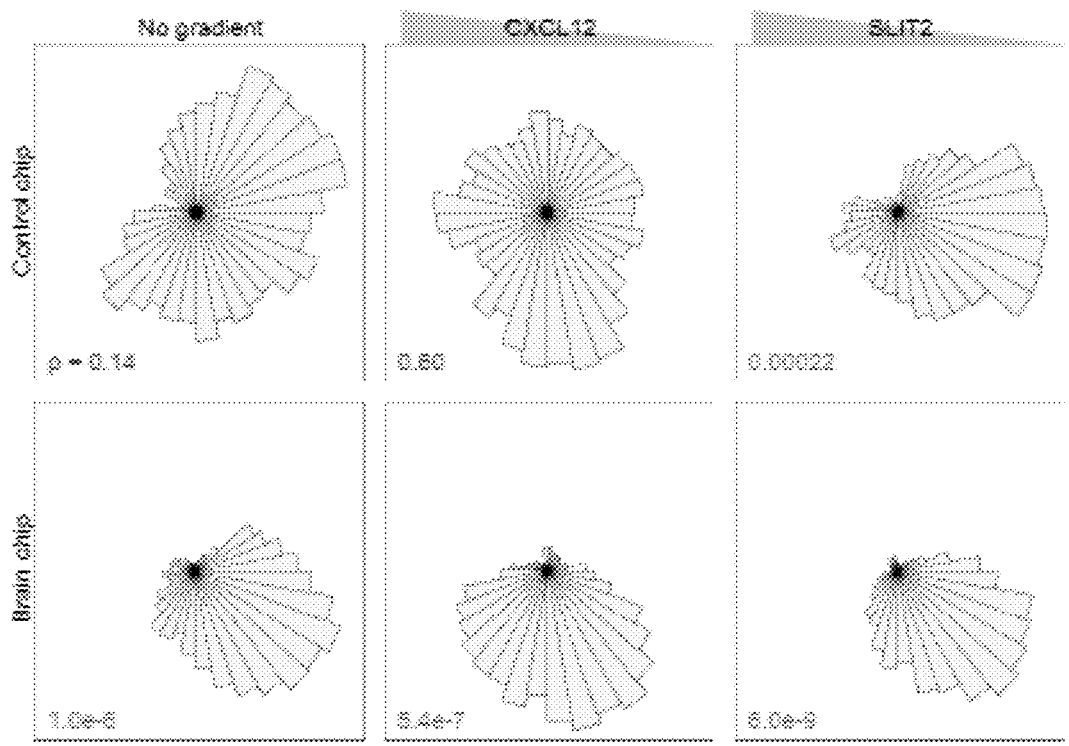
Figure 11E:
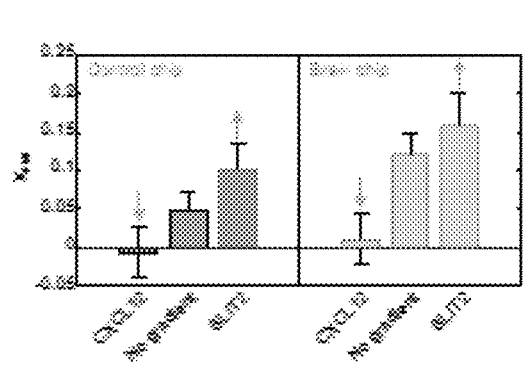
Figure 11F:
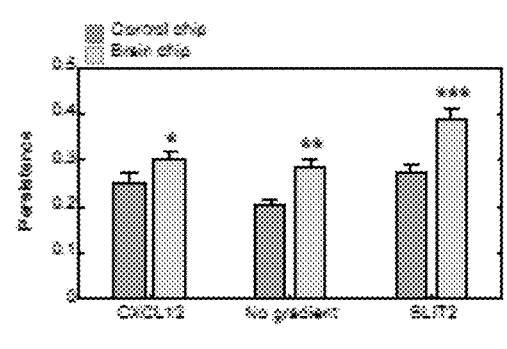

As depicted in FIG. 5, cells are seeded onto surfaces of the top compartment and bottom compartment in various configurations which allows for modeling of tissue. In this manner, the device of the present invention may be configured such that it is capable of mimicking characteristics of functional organs, such as lung and brain. This is accomplished by seeding the membrane 40 and/or compartments of the device with one or more types of living biological cells.

Virtually any type of cell may be used for seeding the device depending on the tissue or organ to be mimicked. For example, by way of illustration and in no way limiting, such cell types include epithelial, endothelial, smooth-muscle, neural, cardiac, and immune cells. An illustrative list of eukaryotic cell types that can be used includes stem cells; pluripotent stem cells; primary cells; fibroblasts; motile cells, ciliated cells; cancer cells including cervix, ovary, colorectal breast, prostate, bladder, pancreas, kidney, lung, salivary gland, testis, cecum, liver, colon, mammary gland, vulva, stomach, pleura, bladder, brain, bone, bone marrow, lymph, eye, connective tissue, pituitary gland, muscle, heart, spleen, skin, uterus, endometrium cells, epithelial cells; endothelial cells; blood cells; neural cells; secretory cells including adrenal gland cells; contractile cells including smooth muscle cells and skeletal muscle cells; hepatocytes; adipocytes; lymphocytes; macrophages; T-cells; B-cells; dendritic cells; neurons; chrondrocytes, and stem cells including embryonic, fetal, amniotic, adult and induced pluripotent stem cells. Examples of some cell types listed above include Swiss 3T3, NIH 3T3, MDA-MB-231, MCF-7, HEPG2, CHO, CACO-2, MDCK, B16-F1, B16-F10, HUVEC, PC-12, WI-38, HDF, and SW-13 cell lines.

The cells may be cultured within the device in gas and/or liquid fluid culture medium. Many commercially available media such as Dulbecco's Modified Eagles Medium (DMEM), RPMI 1640, Fisher's, Iscove's, and McCoy's, may be suitable for supporting the growth of the cell cultures. The medium may be supplemented with additional substances such as salts, carbon sources, amino acids, serum and serum components, vitamins, minerals, reducing agents, buffering agents, lipids, nucleosides, antibiotics, attachment factors, and growth factors. Formulations for different types of culture media are described in various reference works available to the skilled artisan (e.g., Methods for Preparation of Media, Supplements and Substrates for Serum Free Animal Cell Cultures, Alan R. Liss, New York (1984); Tissue Culture: Laboratory Procedures, John Wiley & Sons, Chichester, England (1996); Culture of Animal Cells, A Manual of Basic Techniques, 4th Ed., Wiley-Liss (2000)).

In one embodiment, the top side of the membrane 40 is coated with airway-derived epithelial cells, while a surface of the bottom compartment 25 (i.e., surface 35) is coated with airway-derived smooth-muscle cells as discussed further in Example 4. Such a configuration allows lung tissue to be mimicked. In this embodiments, the platform is the first of its kind that allows quantitative measurements of airway smooth-muscle cell responses in a chip platform in the presence of airway epithelial cells. The platform further allows application of a controlled pressure on the epithelial cells to induce compressive or tensile stress on the cells. This stress models various mechanical aspects of bronchospasm, and therefore allows the investigation of how airway epithelium and smooth-muscle interact.

The device technology can be used to analyze other human conditions in a similarly quantitative manner. For example, in a related manner, the top side of the membrane 40 is coated with endothelial cells, while the bottom compartment is coated with neuronal progenitor cells, e.g., NT2 cells. Such a configuration allows brain tissue to be mimicked.

A device of the present invention may also incorporate other physical, chemical, or electronic components necessary or desirable for a given objective of the cell culture. For example, it may be connected to other apparatuses and/or instruments for proper operation of the culturing processes, as would be apparent to and understood by a person skilled in the art of bioprocess engineering. In one embodiment, the system may further include a fluid or exchange apparatus to exchange or modify the culture medium in the bulk or within the top and/or bottom compartments manually or automatically. For example, the device may include one or more access ports 75 or opening 70 as shown in FIG. 1 to provide access to the top or bottom culturing environments.

In embodiments, one or more of the access ports or opening may be configured such that a stimulus may be provided to the cells being cultured in the top and/or bottom compartments. In one embodiment, one or more of the access ports is fluidly connected to a gas source such that pressure may be introduced into the top and/or bottom compartment thereby providing a compressive stress on cells within the system. As such, the present invention provides a method for performing a biological assay using the microphysiology device of the disclosure. The method includes providing a device of the disclosure, wherein at least one side of the membrane and the bottom compartment are coated with living cells; applying a stimulus to the cells; and monitoring the cells in response to the stimulus which may be physical, chemical, or biological in nature.

In embodiments, the stimulus is an electromagnetic field which applies a force upon magnetic particles attached to cells in the top and/or bottom compartment. For example, the invention includes applying a magnetic field in the horizontal direction to magnetize the magnetic beads attached to cells in the bottom compartment; and monitoring behavior of cells in the bottom compartment by applying a magnetic field oscillating in the vertical direction that forces the magnetic beads into a twisting motion. In embodiments the horizontal component of the twisting motion is recorded using a microscope imaging the magnetic beads.

The present invention also provides a method for determining an effect of at least one stimulus on cells within the microphysiology device of the disclosure. The method includes applying a stimulus to the top compartment, bottom compartment, or both, wherein the stimulus is physical, chemical, or biological in nature; and monitoring behavior of cells in the bottom compartment. In embodiments, monitoring includes assaying secretion and biochemical activity profiles, microrheological characteristics, or mechanical properties of the cells.

In one embodiment, the physical stimulus is an application of air pressure to the top compartment at a level between about 0 to 100 cm $H_2O$ to cause compressive stress on the cells attached to the membrane.

In another embodiment, a biological molecule may be applied as a stimulus. Such stimuli may include one or more ligands, such as drugs or drug candidates, natural compounds, toxins, smoke, allergens, molds, pollen, nanoparticles, mineral dust, nucleic acids, viruses, bacteria, microbes, cells, hormones, growth factors, and cytokines.

To promote cellular attachment and growth of seeded cells, components of the device, such as the top compartment, bottom compartment, and/or membrane, may further be coated with one or more cellular attachment molecules. Such molecules include collagen, fibronectin, laminin, poly-D-lysine, poly-L-ornithine, proteoglycan, vitronectin, polysaccharide and combinations thereof.

In various embodiments the culture plate and sample well may be formed from a material which is compatible with cells; e.g., biocompatible. Suitable materials can include, glass, ceramics, metals, plastics, polymers including, but not limited to polystyrene, polycarbonate, polypropylene or polymeric thin films.

In various embodiments one or more surfaces of the top or bottom compartments may be coated with a suitable culture substrate the promotes cell adhesion. Likewise, the porous membrane may be coated. In embodiments, the substrate can be formed from, but is not limited to, one or more of collagen, laminin, fibronectin, Matrigel™, agarose, or agar. In some embodiments, the substrate is formed from one or more of collagen, including, for example, type I collagen and/or type IV collagen, and fibronectin. Different concentrations of the substrate material may be utilized to alter the substrate properties. In various embodiments the substrate includes one or more of a polypeptide, entactin, glycoprotein, collagen, fibronectin, laminin, poly-D-lysine, poly-L-ornithine, proteoglycan, vitronectin, polysaccharide, hydrogel, and combinations thereof.

The compartments of the device may also include three-dimensional culture surfaces. Such surfaces may have interstitial spaces for attachment and growth of cells into a three dimensional tissue. The openings and/or interstitial spaces of the framework in some embodiments are of an appropriate size to allow the cells to stretch across the openings or spaces. Maintaining actively growing cells stretched across the framework appears to enhance production of the repertoire of growth factors responsible for the activities described herein. Any shape or structure that allows the cells to continue to replicate and grow for lengthy time periods may function to elaborate the cellular factors in accordance with the methods herein.

In some embodiments, the three dimensional culture surface is formed from polymers or threads that are braided, woven, knitted or otherwise arranged to form a framework, such as a mesh or fabric. The materials may also be formed by casting of the material or fabrication into a foam, matrix, or sponge-like scaffold. In other aspects, the three dimensional framework is in the form of matted fibers made by pressing polymers or other fibers together to generate a material with interstitial spaces. The three dimensional framework may take any form or geometry for the growth of cells in culture. Thus, other forms of the framework, as further described below, may suffice for generating the appropriate conditioned medium.

A number of different materials may be used to form a culture substrate of the device. These materials include non-polymeric and polymeric materials. Polymers, when used, may be any type of polymer, such as homopolymers, random polymers, copolymers, block polymers, coblock polymers (e.g., di, tri, etc.), linear or branched polymers, and crosslinked or non-crosslinked polymers. Non-limiting examples of materials for use as scaffolds or frameworks include, among others, glass fibers, polyethylenes, polypropylenes, polyamides (e.g., nylon), polyesters (e.g., dacron), polystyrenes, polyacrylates, polyvinyl compounds (e.g., polyvinylchloride; PVC), polycarbonates, polytetrafluorethylenes (PTFE; TEFLON), thermanox (TPX), nitrocellulose, polysaacharides (e.g., celluloses, chitosan, agarose), polypeptides (e.g., silk, gelatin, collagen), polyglycolic acid (PGA), and dextran.

The cells may be cultured for any duration of time appropriate for forming a particular tissue structure. In embodiments, cells are culture from about 2 to 12 days, for example, between about 3 to 7 days, 4 to 7 days or 5 to 6 days.

During the incubation period, the cultured cells grow and expand on the culture substrate. The growing cells may produce a myriad of growth factors, regulatory factors and proteins, some of which are secreted in the surrounding media, and others that are deposited on the support along with the cells. Growth and regulatory factors can be added to the culture during incubation to induce differentiation of the cells to the desired cell type.

Culture conditions are typically under appropriate conditions of pH, temperature, and gas (e.g., $O_2$, $CO_2$, etc) to maintain a growth condition suitable for the particular tissue being mimicked. In some embodiments, the cell culture can be grown in monolayers on either or both sides of the membrane as well as in the bottom compartment. In addition, the culture may be "fed" periodically to remove the spent media, depopulate released cells, and add new nutrient source.

In order to determine the amount of a particular type of a cell in a cell culture or cell population, a method of distinguishing this cell type from the other cells in the culture or in the population may be used. Accordingly, in one embodiment, the methods further relate to cell markers whose presence, absence and/or relative expression levels are specific for specific cell types. As used herein, "expression" refers to the production of a material or substance as well as the level or amount of production of a material or substance. Thus, determining the expression of a specific marker refers to detecting either the relative or absolute amount of the marker that is expressed or simply detecting the presence or absence of the marker. As used herein, "marker" refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipid, a lipid, a lipoprotein or a small molecule.

In various embodiments, access ports and openings may be made using a variety of techniques known in the art. For example such techniques may include, but are not limited to, machining, drilling, milling, laser machining, punching, die casting, molding, etching, and the like.

One or more of the culture surfaces, for example the porous membrane and/or the bottom compartment, may be derivatized or coated before or during culture with extracellular matrix molecules, adhesion ligands, growth factors, receptors, and the like as discussed herein. The use and benefits of coating the surfaces of a culture chamber is known to a person skilled in the art.

As can be appreciated, cells can attach to the surfaces they contact. The culture surfaces may also be modified or coated to increase affinity to a certain cell type to control the cell growth. When the surfaces have no or little affinity to the cultured cells, the cultured cells may be confined but do not attach to the surfaces, and thus they are mobile and may move laterally along culture surfaces before establishing the tissue structure. For example, cells may move due to a concentration gradient of a substance in the culture medium or they may be forced to move by an external force such as a magnetic force. Cells may orient in a certain way depending on the surface properties. The surface materials may also be so selected as to test compounds that attract or repel a certain cell.

The culture surfaces of the device may be made reactive so that other molecules may be covalently linked. The surface can be made reactive in various ways known to those skilled in the art, for example by treatment with such molecules as aminopropyltrimethoxysilane (APTS), which presents amine groups on the surface. Thin layers or bulk materials may be linked to the surface. Bulk materials include gels made from protein, polyacrylamide, or other materials. Such gels may be formed in molds made with standard microfabrication techniques. The gels may be placed on the surface and covalently bound into place by reaction with the activated surfaces. For example, collagens or fibronectin may be used.

The surfaces may be derivatized with binding proteins that a target cell type is normally exposed to in a natural environment, such as claudin and occludin (for tight junctions), cadherins (for actin-linked, adherens junctions), co unexins (for gap junctions), and selectins (for selectin-lectin interactions)). Thin layers of proteins may be patterned on the surfaces, for example by treatment of the APTS-treated surface with glutaraldehyde, or with the photoactivatable cross-linker 4-benzoylbenzoic acid succinimidyl ester, or by using other techniques known to those skilled in the art. The proteins may be of any type. The proteins may be patterned in concentration gradients on surfaces by methods known to those skilled in the art.

A control system such as a computer or other automation devices (not shown in the figures) may be used to monitor and control the operation of the device, and to analyze obtained data. The culturing environment in the top or bottom compartments may be adjusted dynamically based on the information gathered in real time. Media flow and metabolite concentrations can be monitored and controlled.

For example, sensors may be connected to the control system using electrodes and may be used to simultaneously measure the concentration of oxygen and the pH value in the culture spaces. Further, with multiple sensors, the gradient of a given material in the chamber can be measured. Feedback information may include values of pH, glucose and oxygen concentrations, temperature, osmolarity, shear forces, and the like.

Electrical conductors may be embedded in the device for connecting sensor and pump electrodes to external electronics and power sources. The conductors may be deposited using standard microelectronics fabrication techniques. For example, the conductors may have a thickness on the order of nanometers. A conductor may run along the surface of a substrate or through the substrate. Conductors may also be covered with inert coatings with non-conducting materials such as aluminum oxide.

As mentioned earlier, computers and computer programs can be used to control the culturing and monitoring of cells and to analyze obtained data. Microprocessors can be incorporated into the device or in a separate centralized unit. The computer system can record the measurements from the sensors, analyze the data, and control the culture parameters accordingly. The culture chamber and accessory devices may be monitored and controlled by one or multiple processors and software programs. For example, the system may be programmed to apply a magnetic field to cells in the device or monitor such cells.

In another aspect, the present invention provides a method of fabricating a microphysiology device of the disclosure. The method includes attaching a polydimethylsiloxane structure to a polycarbonate or polyester membrane. Attachment includes exposing the polydimethylsiloxane structure and the membrane to an oxygen plasma to chemically activate their surfaces; wetting the surface of the polydimethylsiloxane structure, the membrane, or combination thereof, with a bonding solution of 1% (3-Aminopropyl) triethoxysilane in water after plasma treatment; and contacting the polydimethylsiloxane structure with the membrane to cause permanent bonding upon evaporation of the water in the bonding solution.

The following examples are provided to further illustrate the embodiments of the present invention, but are not intended to limit the scope of the invention. While they are typical of those that might be used, other procedures, methodologies, or techniques known to those skilled in the art may alternatively be used.

Example 1

Organ-Chips for Modeling Asthma

Asthma is an international health problem of epidemic proportions that affects around 300 million people worldwide with an estimated 250,000 annual deaths. The major source of morbidity and mortality of asthma is airway obstruction, which often is due to actively constricted smooth muscle of the bronchi or remodeling of connective tissue due to chronic inflammation. In addition, asthma morbidity is also attributable to the relatively slow recovery from bronchospasm. A better understanding of the factors that contribute to airway smooth muscle contraction and/or its delayed relaxation has a potential for better treatment for airflow obstruction in asthma.

Animal models of asthma face increased scrutiny and are questioned with regards to their validity because of markedly discrepant experimental findings and disagreement between animal and human studies. Studies using tissues obtained from postmortem or surgical specimens have their own limitations and, moreover, obtaining donor lungs of asthmatics unsuitable for transplantation is rare, and sporadic at best, making tissue/cell studies not only problematic to do but also difficult to time. To address these problems, the inventors have developed a biomimetic in-vitro platform that reconstitutes physiological and mechanical aspects of an asthmatic airway. For these studies, primary cells were prepared from donor lungs procured from the National Disease Research Interchange and the International Institute for the Advancement of Medicine. Using these airway epithelial cells and smooth muscle cells, a 3D co-culture model was constructed. This asthma platform allows measurement of changes in tissue stiffness and smooth muscle contraction. These measurements are done using magnetic twisting cytometry to probe changes at the cellular level. This platform will complement current animal studies and allow a much more extensive drug and toxin screen using human tissues.

This technology platform was used to study asthma and associated bronchospasm. The platform reconstituted mechanical and biochemical aspects of the airways, and showed that a compressive stress on airway epithelium leads to secretions that contract airway smooth muscle, thereby reinforcing bronchospasm. The PDMS-based device used in this study consisted of a human airway epithelial layer in an air-liquid interface, and a human airway smooth muscle layer, separated by a perforated membrane. A pressure gradient was introduced to the upper layer of the organ-chip, so that epithelial cells experienced compressive stresses similar to physiological levels encountered during bronchospasms. To measure the biomechanical effects of the secretions caused by this compressive stress on smooth muscle cells, contraction or relaxation in the smooth muscle layer was measured using magnetic beads introduced into the bottom layer of the chip. Absolute and relative stiffness and their change over time were then quantified using optical magnetic twisting cytometry.

Example 2

Organ-Chips for Modeling Brain Cancer

Glioblastoma multiforme is one of the most lethal cancers and the most common primary brain tumor in adults. Despite multimodal treatment, such as local radiation therapy, systemic chemotherapy, and surgical resection, glioblastoma displays characteristic recurrence, followed by swift fatality typically within one year after diagnosis. One of the difficulties in treating glioblastoma stems from the difficulty in delivering drugs through the blood-brain barrier (BBB). The use of mesenchymal stem cells shows enormous therapeutic potential for brain tumor therapy, since these cells are able to transmigrate through the BBB and show a natural affinity for tumors. In our research, these stem cells are isolated from human fat tissue, grown to expand to the numbers required for the application, and genetically modified to better target glioblastoma tumors.

To test the therapeutic potential of enhanced mesenchymal stem cells, a brain-on-a-chip platform was developed that reconstitutes the functionalities of the BBB and the brain microenvironment. The device is compartmentalized into a vascular layer and a brain layer, separated by a BBB. Glioblastoma cells are seeded into the brain layer to observe how modified mesenchymal stem cells target the tumor area, and test for possible detrimental differentiation in the stem cells. Besides standard phase-contrast and fluorescence microscopy, the platform also allows measurements through incorporation of various sensors to measure, for example, electrical resistance to probe the permeability of the BBB in response to inflammatory signals. This platform may also be utilized for migration, proliferation, invasion, and differentiation studies in various brain cancer types.

Additional results and embodiments of the device used in this Example are depicted in FIGS. 6-9.

Example 3

Fabrication

The device utilized in Example 1 was fabricated as follows.

The lung-chips were fabricated using a flexible and optically transparent polydimethylsiloxane (PDMS) polymer, using standard soft lithography techniques, whereby the liquid polymer is poured over a master and cross-linked at 80° C. for 2 hours. The master for the chips was fabricated using optical lithography using an epoxy-based negative photoresist (SU8) that yields thick and robust structures. The chips consist of two identical PDMS compartments, each having channels with 5 mm width, 20 mm length, and 300 µm height, and around 100 support pillars with 200 µm diameter distributed across the channels. The two compartments are separated by an optically clear polycarbonate membrane with 5 diameter holes, allowing cells on both sides of the membranes to chemically interact.

To construct the complete chip, first a PDMS compartment and the polycarbonate membrane are exposed to an oxygen plasma (30 W, 700 mTorr, 30 sec) to chemically activate their surfaces. Immediately after the plasma treatment, the PDMS surface is silanized using 5 µl of an APTES solution (1% (3-Aminopropyl)triethoxysilane in water) and the polycarbonate membrane is bonded to it. After 2 hours of bonding, the process is repeated to bond the second PDMS compartment to the polycarbonate structure and complete the lung-chip. The chip is further bonded to a glass coverslip for support.

After the chip is sterilized under intense UV light, the two compartments are coated with collagen and subsequently seeded with primary human airway epithelial cells and primary human airway smooth muscle cells, respectively. This platform allows measurement of changes in tissue stiffness and smooth muscle constriction. The measurements are performed using both a pressure setup that can apply compressive stress on epithelial cells, and using magnetic twisting cytometry to probe mechanical changes on smooth-muscle cells at a single-cell level.

Example 4

Mechanotransduction-Mediated Feedback as a Possible Mechanism for the Acute Persistence of Bronchospasm Mechanisms that sustain extended episodes of bronchospasm in asthmatic airways are not clear. Due to a lack of models that recapitulate airway function, progress in this area has been primarily driven by organ-level or molecular-scale studies that predict bistable systems based on purely mechanical or biochemical considerations. The anatomy of the bronchi, however, suggests a milieu of interacting mechanical and biochemical signals that could shape the dynamics of bronchospasm. In this example, the inventors present a tractable microphysiological bronchi-on-a-chip model that allows quantitative analysis of these interactions. It is shown herein that compressive stress at physiological levels on airway epithelial cells leads to strong contraction in smooth muscle cells that manifests itself within minutes, suggesting positive feedback during bronchospasm. This contractile effect is maintained over extended durations through the discordant regulation of cyclooxygenase isozymes by compressive stress, relayed via the mechanosensor and transcriptional coactivator Yes-associated protein. These results, therefore, suggest a novel mechanism of irreversible bronchospasm, based on the feedback between airway smooth muscle contraction and activation of inflammatory pathways through mechanical stress in the airway epithelium.

The airways constitute a complex biological network. Under the right combination of external stimuli, a healthy biological network can be pushed to and trapped in a stable pathological state from which a spontaneous return to normalcy may not be possible. A major problem in asthma is extended episodes of bronchospasm, where symptoms persist even when stimuli leading to it are removed. Dissecting the precise mechanisms causing this memory effect is difficult, as it involves interdependent phenomena at multiple length scales. Bistability that can lead to a memory effect in the airways has been reported to exist at different biological scales ranging from the organ level due to emergent phenomena within a bronchial tree, to the molecular level due to MAPK/ERK signaling. At the intermediate level of a single airway, bistability has been proposed by several models based on the interplay between airway smooth muscle (ASM) contraction and airway wall mechanics. These models, however, simplify the airway wall into a passive mechanical element. The anatomical structure of the bronchi suggests a more active role for the airway wall. For example, it has been suggested that stimulation of irritant receptors in the airways during bronchospasm could activate a vagal positive feedback loop. Here, the inventors provide evidence for a similar feedback based on the interaction of the epithelium and ASM via paracrine signaling and mechanosensing.

When bronchospasm is triggered through environmental insults, the ASM compresses the airway and causes mucosal folding. During this process, the mucosa forms deep crevasses, exposing the epithelium to considerable compressive stresses. Several studies show mechanical stress in various forms regulate the release of epithelium-derived factors, including ATP at short time scales (seconds) and eicosanoids at longer time scales. ATP is a spasmogen that acts through purinergic receptors on ASM cells and eicosanoids influence both relaxation and contraction. This points to a complex feedback between the epithelium and ASM, mediated by paracrine signaling and mechanotransduction in a wide range of time scales. When the positive component of this feedback dominates so that the contracted ASM state can be maintained exclusively by the feedback, bistability can lead to irreversibility, i.e., trapping of the system in the aberrant stable state even after removal of external stimuli that trigger the bronchospasm.

Experimental models to investigate this proposed effect are lacking. While ex vivo models such as lung slices reproduce some of the required complexities, it is difficult to control conditions in these systems and even more difficult to extract information with high fidelity or in a quantitative manner. A highly controlled in vitro environment that recapitulates important aspects of the interplay of chemical and mechanical transduction would provide more precise information towards a mechanistic understanding of this proposed feedback. In this study, a tractable in vitro model is utilized to perform mechanistic studies of bronchospasm, and a new mechanism of bistability is proposed based on the feedback between ASM contraction and activation of inflammatory pathways through mechanical stress in airway epithelial cells.

RESULTS

Microphysiological Airway Model Results Indicate Positive Feedback Between Smooth-Muscle Contraction and Compressive Stress on Epithelium [=>Actual Result is: Compressive Stress on Epithelium Leads to Strong Contraction of ASM].

Figures 12A, 12B, 12C, 12D:
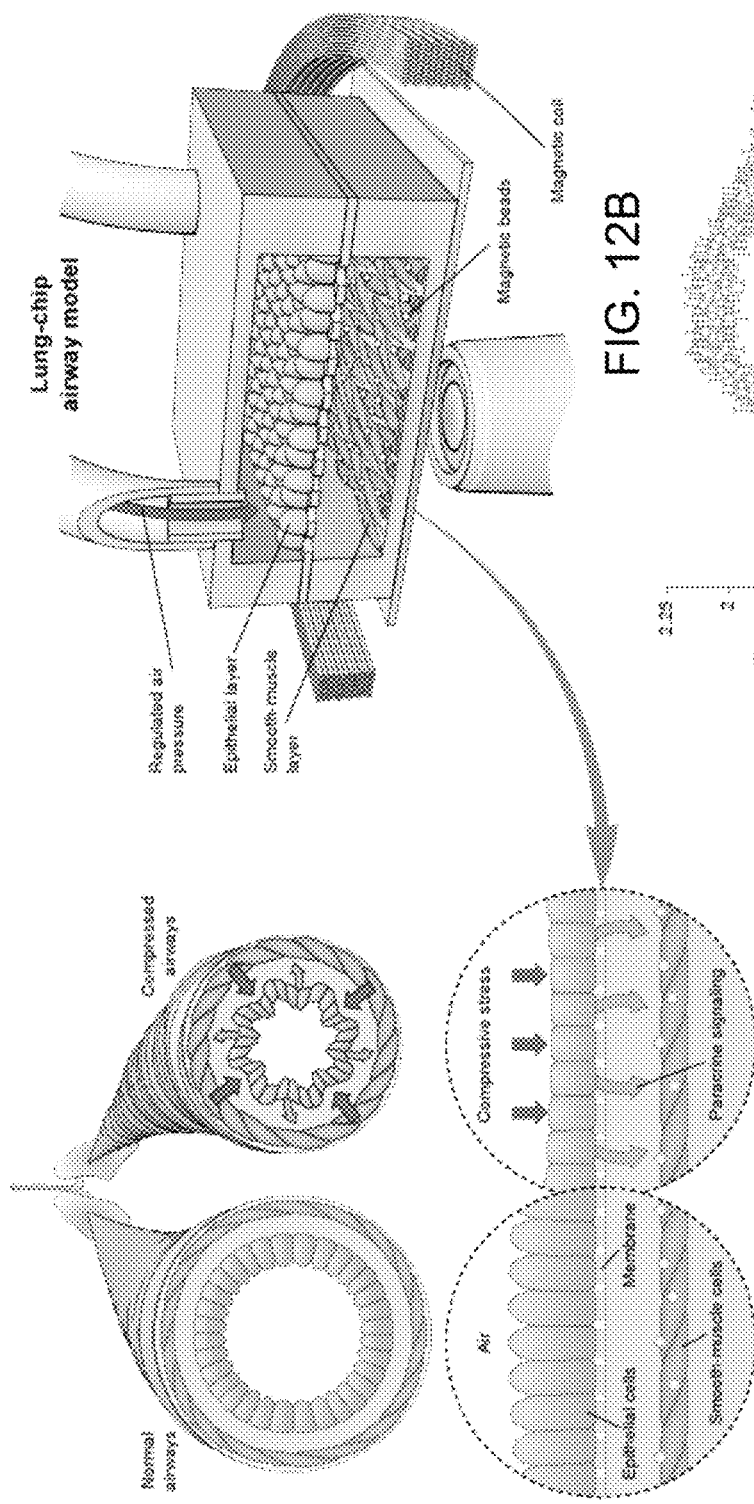
FIGS. 12A-12D are a series of schematic and graphical representations of a microphysiology device for modeling respiratory disorders in embodiments of the invention as well as experimental data generated using the device.
Figure 18A:
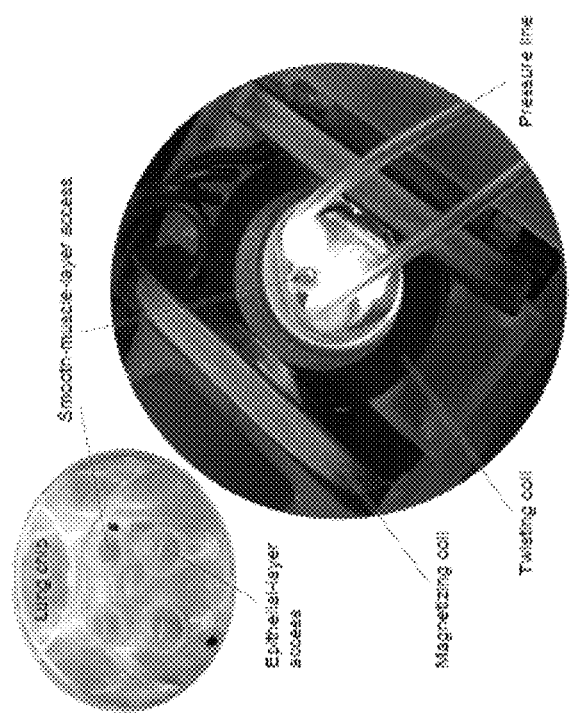
FIGS. 18A-18E are a series of schematic representations relating to a microphysiology device in embodiments of the invention.
Figure 18B:
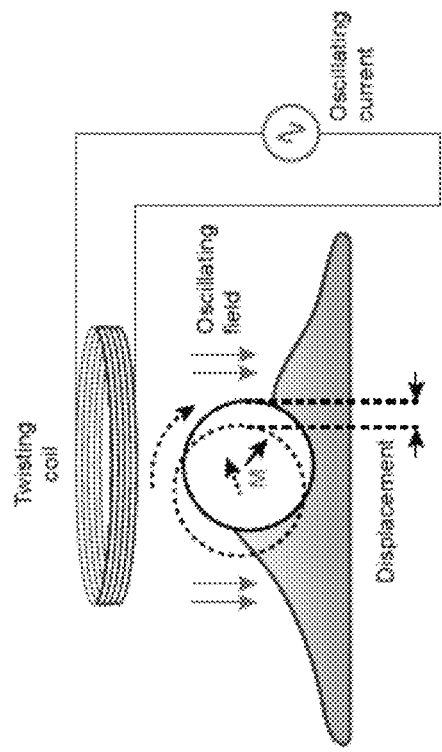
Figure 18D:
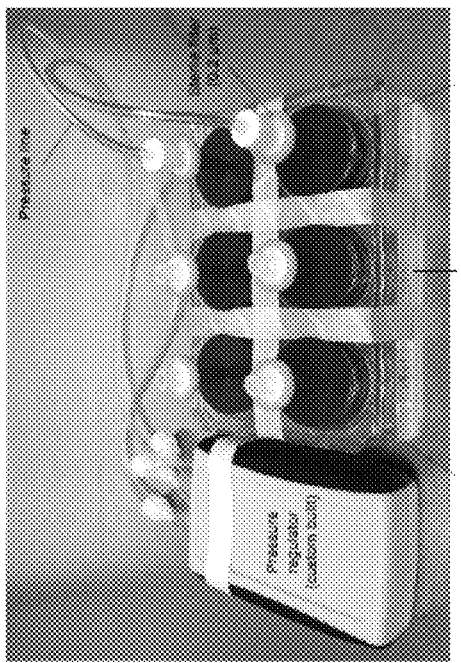
Figure 18C:
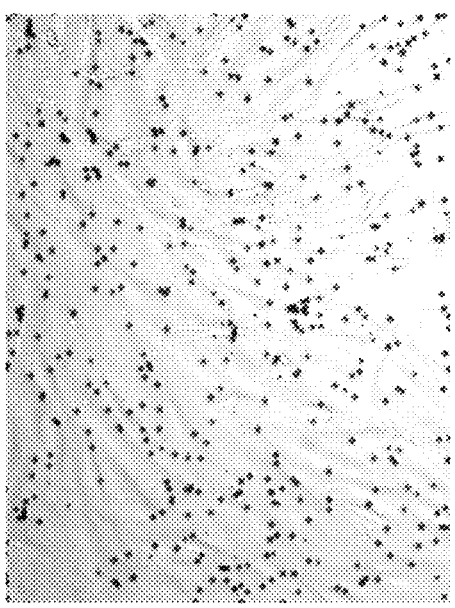

Animal models or surrogates such as ex vivo lung slices do not provide sufficiently controlled environments that allow a quantitative analysis of the hypothesized feedback. To address this, a microphysiology device of the invention (also referred to herein as a lung-chip) configured as an airway model was utilized, that reconstitutes 3D co-cultures of early-passage primary human ASM and airway epithelial cells that are fully-differentiated in an air-liquid interface. The lung-chip allows the application of an apical-to-basal compressive stress mimicking severe bronchospasm and is designed to be compatible with Optical Magnetic Twisting Cytometry (OMTC), a high throughput method for quantitative analysis of in vitro cellular mechanics (FIGS. 18A-C). Using this microphysiological model, it is possible to test how the mechanical stress on epithelial cells, generated in vivo by the contraction of ASM, leads to paracrine signaling (FIG. 12A). The platform allows the application of compressive stress at physiological levels on pseudostratified human airway epithelial cells through regulated air pressure. Resulting changes in mechanical properties of human ASM cells are then quantitatively measured in real-time using OMTC (FIG. 12B). OMTC utilizes RGD-coated magnetic beads that bind to cell surface integrin receptors, hence allow probing of the actin cytoskeleton (beads on human ASM layer inside lung-chip shown in FIG. 12C). The platform allowed the inventors to observe that an application of 30 $cmH_2O$ compressive stress on the epithelial-cell layer, a stress level observed during severe bronchospasm, leads to strong ASM contraction, whereby cell stiffness changes more than two-fold within two minutes (applied after t=60 seconds in FIG. 12D). This suggests a positive feedback where compressive stress on the epithelium due to ASM contraction leads to the release of epithelium-derived spasmogens.

Feedback Manifests Over Longer Durations Primarily Through Eicosanoid Production.

Figure 13A:
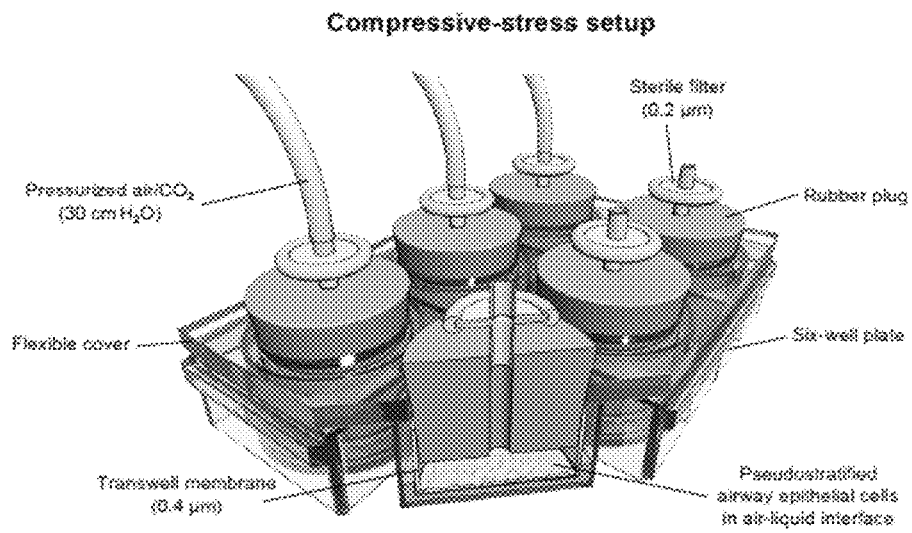
FIGS. 13A-13D are a series of schematic and graphical representations of a microphysiology device for modeling respiratory disorders in embodiments of the invention as well as experimental data generated using the device.
Figure 13B:
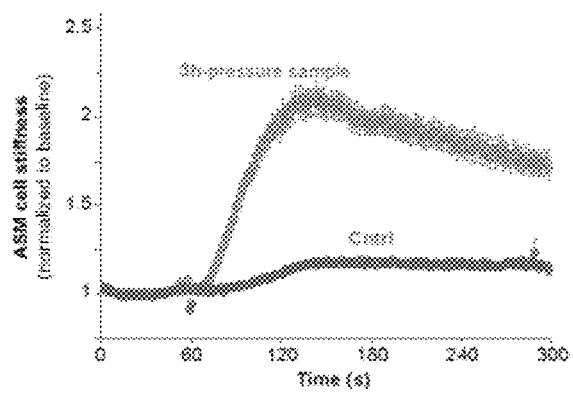
Figure 13C:
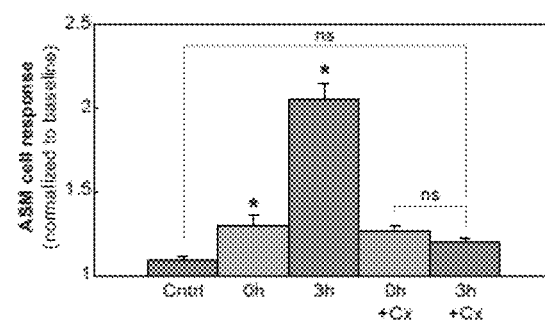
Figure 13D:
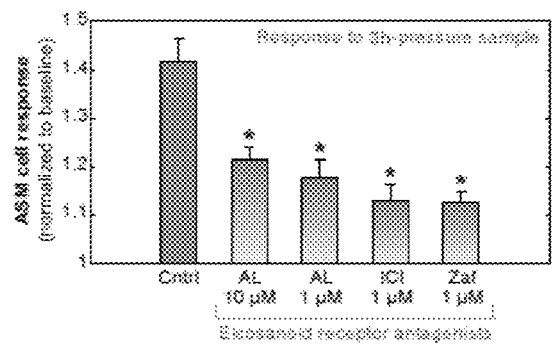
Figure 18E:
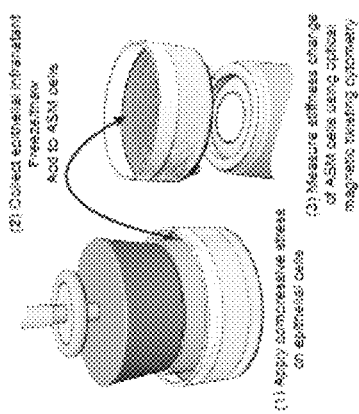

While the lung-chip results indicate the presence of a positive feedback between ASM contraction and epithelial factor release over time scales on the order of minutes, episodes of bronchospasm are typically observed over longer time scales (several hours). To test for the presence of a protracted feedback, a setup that allows analysis of the effects of compressive stress on airway epithelial cells with larger cell numbers was used (FIG. 13A; FIG. 18D). The setup is based on a six-well platform with pseudostratified primary human airway epithelial cells in an air-liquid interface. FIG. 13B shows that the infranatant (the media collected below cells in the air-liquid interface; FIG. 18E) from epithelial cells treated with 3 hours of compressive stress caused strong contraction in ASM cells. Recently it was shown that cyclooxygenase plays a significant role in mechanotransduction. Therefore the inventors further investigated whether the epithelial factors causing ASM contraction include cyclooxygenase products. Application of the COX2 inhibitor Celecoxib suppressed the effects of compressive stress on epithelial cells, as ASM cell contraction in response to no pressure (0h) and 3h-pressure epithelial samples were at similar levels (FIG. 13C). This points towards a critical role for cyclooxygenase, and suggests that prostanoids may constitute a significant portion of the epithelium-derived factors that cause ASM contraction. To validate this, the response of ASM cells treated with different eicosanoid receptor antagonists to the 3h-pressure epithelial infranatant was analyzed, and significant inhibition of the contractile response was observed (FIG. 13D). Overall, these results suggest that a significant contribution to ASM contraction comes from different eicosanoids.

Eicosanoid Production is Regulated by Modulation of Cyclooxygenase Isozymes by Compressive Stress.

Figure 3:
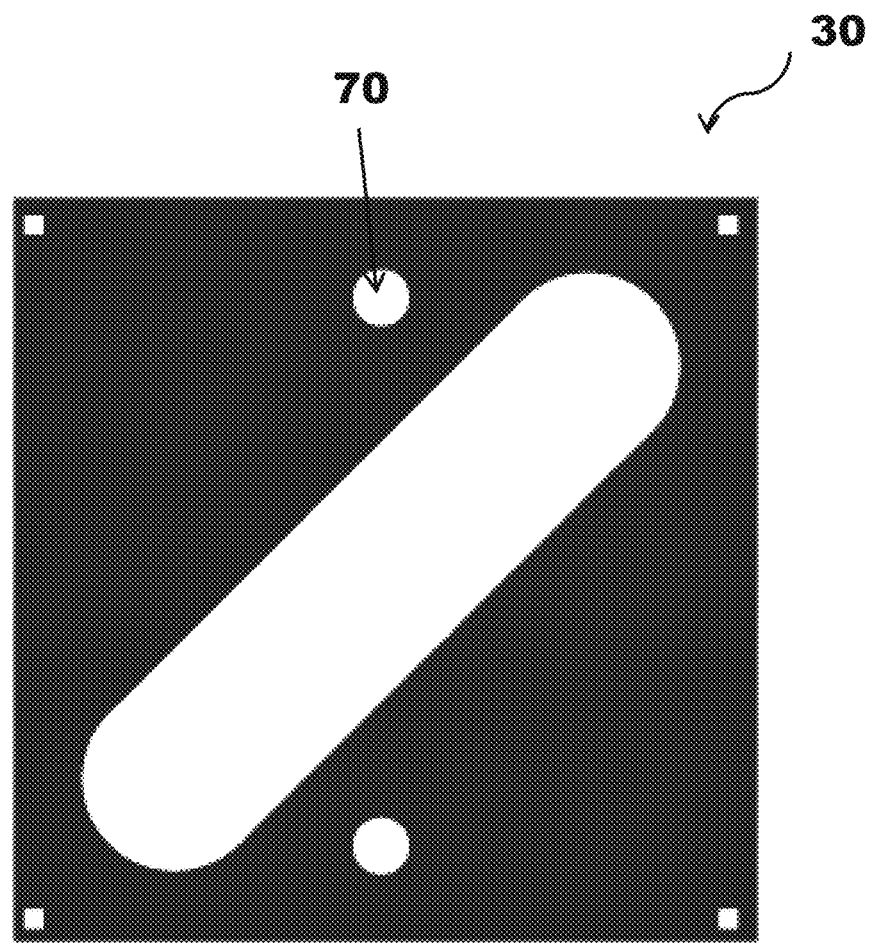
FIG. 3 is a top view of bottom plate 30 according to one embodiment of the invention.
Figure 4:
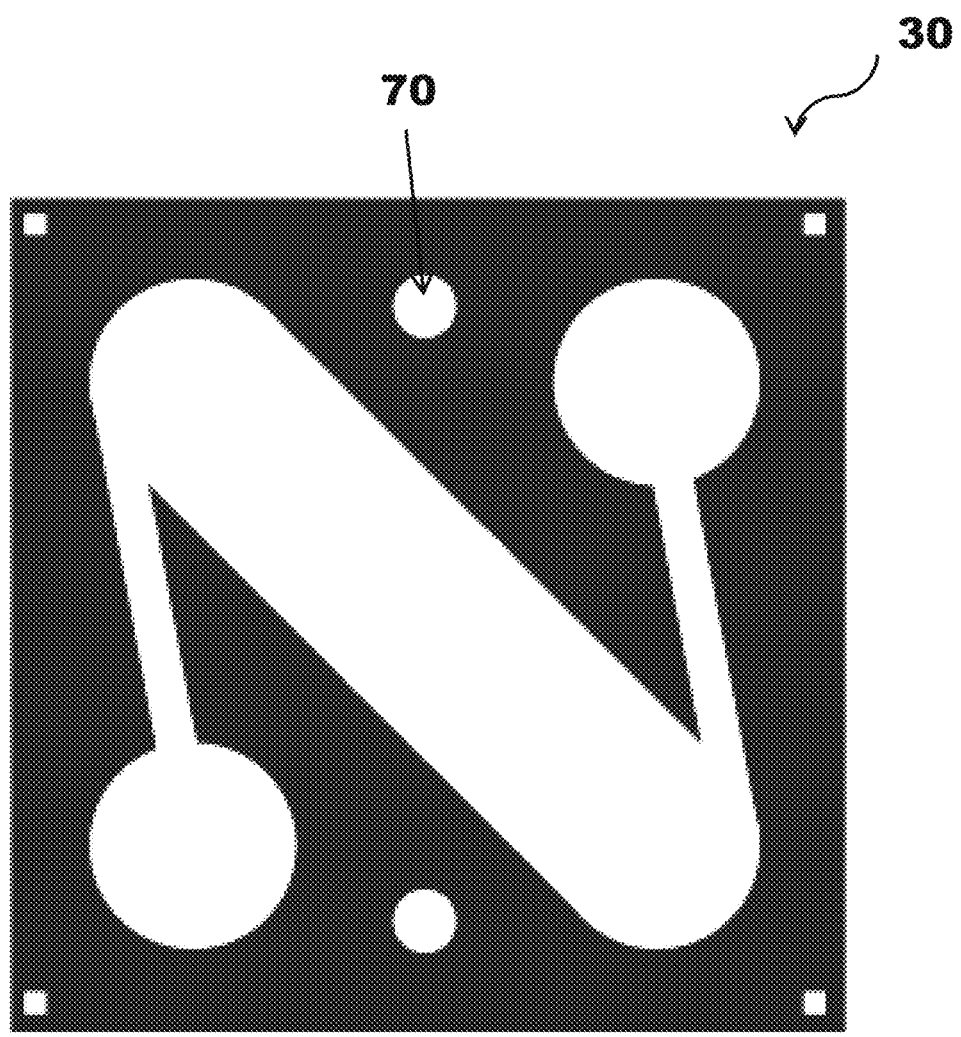
FIG. 4 is a top view of bottom plate 30 according to one embodiment of the invention which is suitable in embodiments when cells in the top compartment require an air or gas environment for extended periods of time.
Figure 14A:
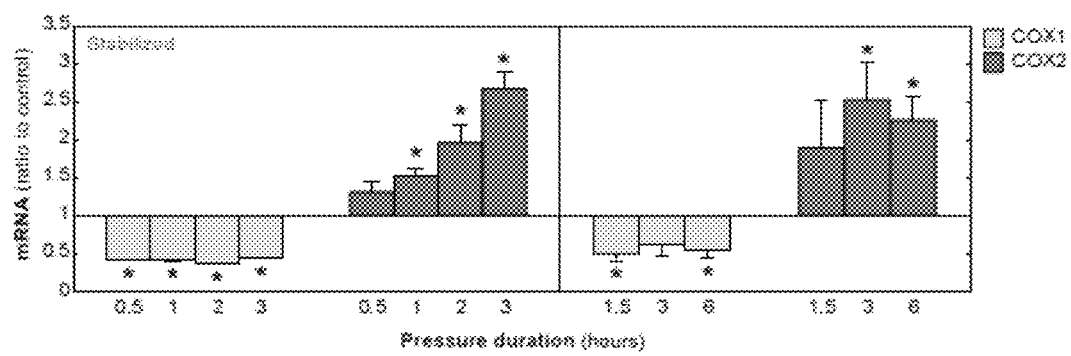
FIGS. 14A-14B are a series of graphical representations depicting data of eicosanoid production in embodiments of the invention.
Figure 19A:
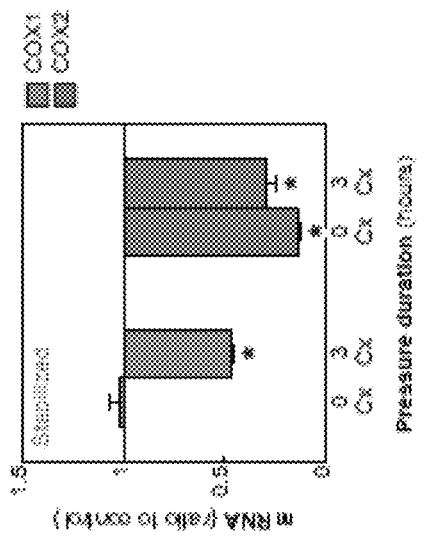
FIGS. 19A-19D are a series of graphical representations depicting data relating to stabilized cells in embodiments of the invention.

To further test the role of cyclooxygenase products, how compressive stress regulates PTGS1 and PTGS2, the genes for the two cyclooxygenase isozymes was analyzed. Following the application of compressive stress on airway epithelial cells, the inventors observed a clearly discordant regulation of these two genes, with PTGS1 (COX1) downregulated at a steady level, and PTGS2 (COX2) upregulated at levels increasing with the duration of the compressive stress (FIG. 3A). It is interesting to note that these results show parallels with aspirin-induced asthma, where COX1-inhibition in sensitive individuals can trigger bronchospasm. To test the effect of this discordant regulation of cyclooxygenase on prostanoid production, the inventors measured the $PGE_2$ content of epithelial infranatants using an ELISA test (FIG. 3B), which showed increasing levels of $PGE_2$ concomitant to COX2 upregulation. $PGE_2$ is known to be involved in a positive feedback mechanism, where $PGE_2$ regulates COX2 through the EP2/4 receptors. This feedback is also evident in FIG. 19A, showing reduced COX2 mRNA expression levels in response to pharmacological COX2 inhibition. Therefore, not letting $PGE_2$ levels stabilize is expected to lead to transient effects. Keeping the epithelial cells in overnight media during the compressive stress experiments provided more consistent results with less sample-to-sample variation (denoted as 'stabilized' in FIGS. 14A-B).

Compressive Stress is Relayed to Cyclooxygenase Through the Mechanosensor YAP.

Figure 15A:
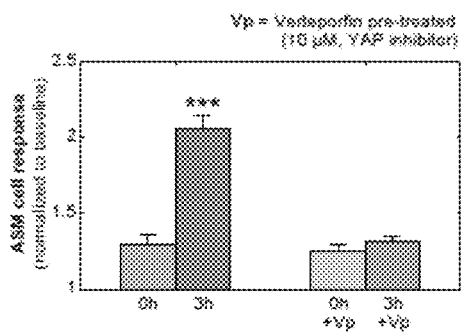
FIGS. 15A-15E are a series of graphical representations depicting data relating to compressive stress in embodiments of the invention.
Figure 15B:
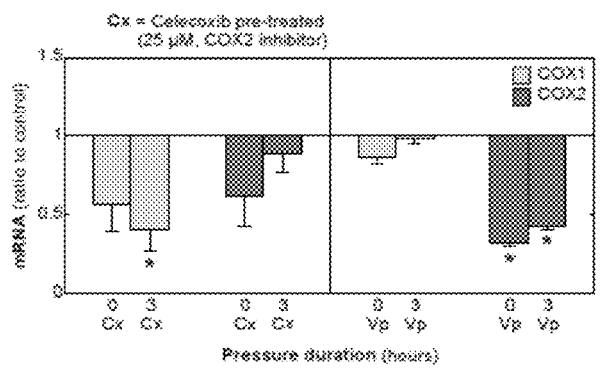
Figure 15C:
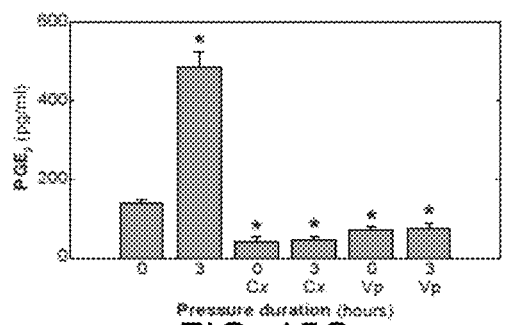
Figure 15E:
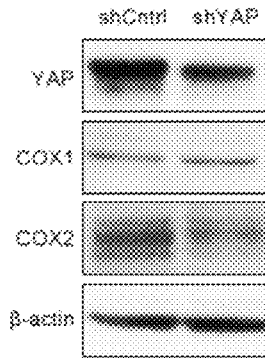
Figure 15D:
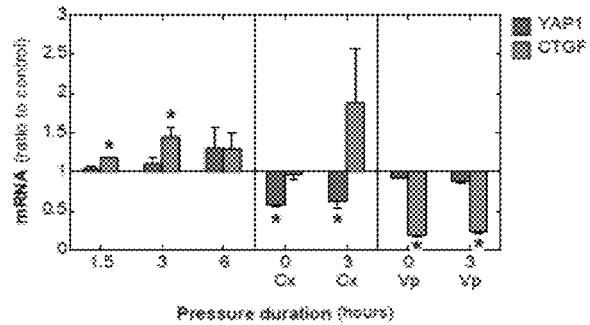
Figure 19B:
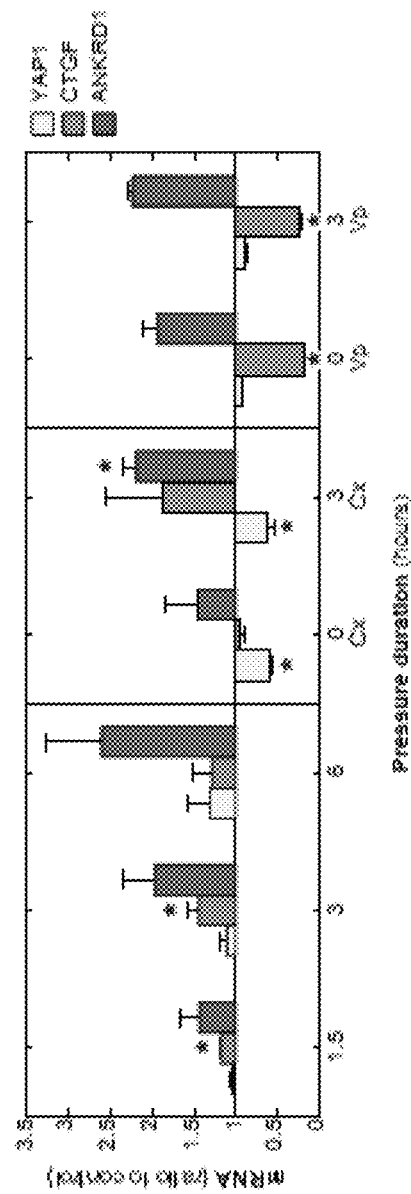
Figure 19D:
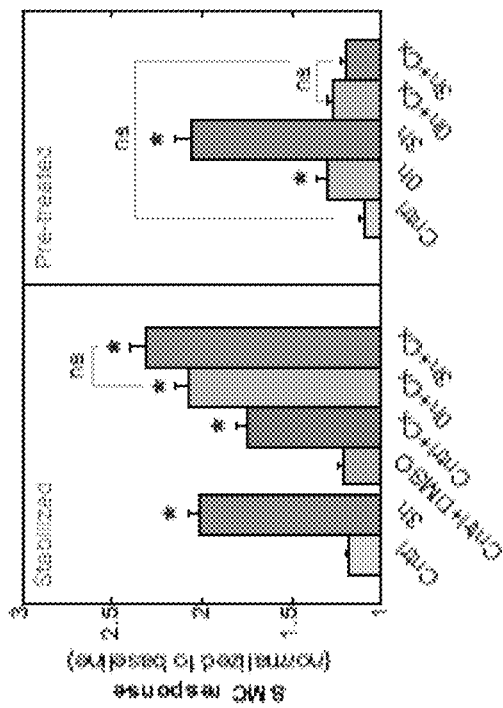
Figure 19C:
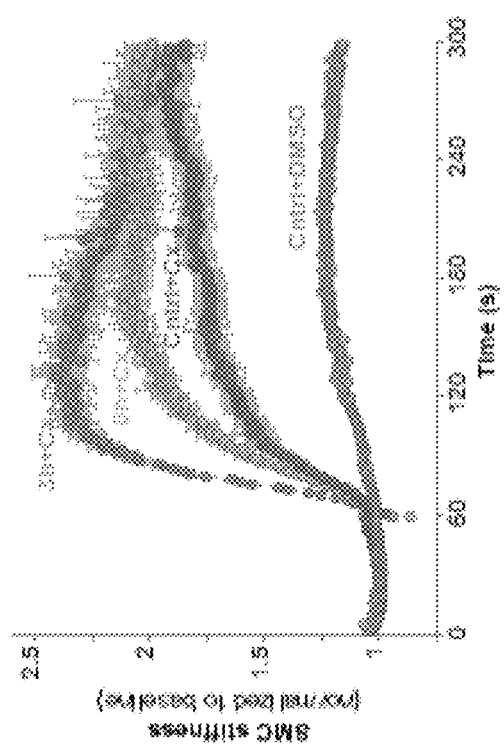

The differential regulation of PTGS mRNA levels by compressive stress indicates transcriptional regulation through a mechanotransduction pathway. Yes-associated protein (YAP) has been implicated as an important nuclear relay of mechanical signals that can be activated by tensions in the actomyosin cytoskeleton and by Rho GTPase activity. The inventors therefore tested ASM contraction in response to infranatant from epithelial cells exposed to compressive stress and/or treated with the pharmacological YAP inhibitor Verteporfin. YAP inhibition abrogated the effects of compressive stress, as ASM cell contraction in response to no pressure (0h) and 3h-pressure samples were at similar levels (FIG. 15A). The role of YAP was further tested by measuring the effect of Verteporfin on PTGS1 and PTGS2 mRNA expression in airway epithelial cells. YAP inhibition downregulated COX2, and prohibited the downregulation of COX1 and upregulation of COX2 by compressive stress (FIG. 15B), consistent with the results in FIG. 15A. The functional relevance of YAP inhibition (and selective COX2 inhibition) was confirmed by measuring the $PGE_2$ content of the infranatants, showing less $PGE_2$ production and suppression of the effects of compressive stress (FIG. 15C). Further support for YAP acting as a mechanosensor for compressive stress came from mRNA expression levels of YAP1 and its target CTGF in epithelial cells (FIG. 15D; FIG. 19B shows results for another YAP target, ANKRD1). The inventors observed that CTGF was upregulated by compressive stress, and this upregulation was abrogated by YAP inhibition with Verteporfin. On the other hand, Celecoxib reduced YAP1 expression, but did not suppress the effect of compressive stress on CTGF. Consistent with these results, it was therefore hypothesized that cyclooxygenase is downstream of YAP. We verified this through Western blots of COX1 and COX2 expression in epithelial cells, following shRNA-mediated knockdown of YAP (FIG. 15E). Collectively, these results showed that ASM contraction can directly trigger feedback loops that could shape bronchospasm dynamics. Therefore, next it was assessed whether there is any difference in the contractility of asthmatic and non-asthmatic ASM cells.

Asthmatic and Non-Asthmatic ASM Cells Have Different Mechanophenotypes.

Figure 16A:
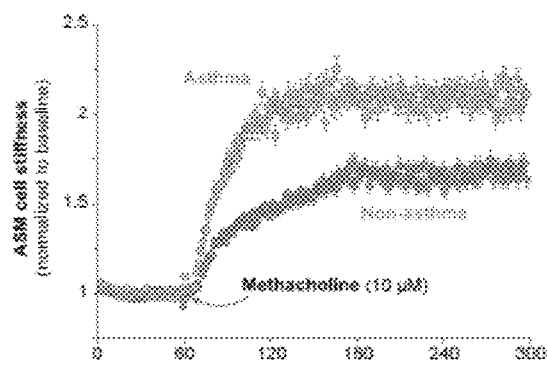
FIGS. 16A-16H are a series of graphical representations depicting data relating to mechanophenotype of cells in embodiments of the invention.
Figure 16B:
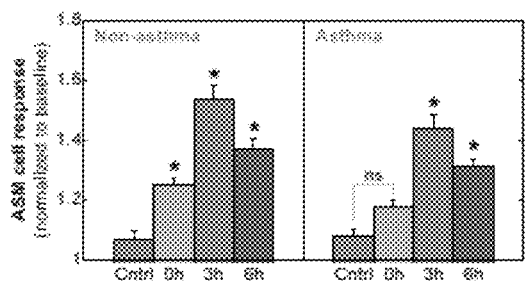
Figure 16C:
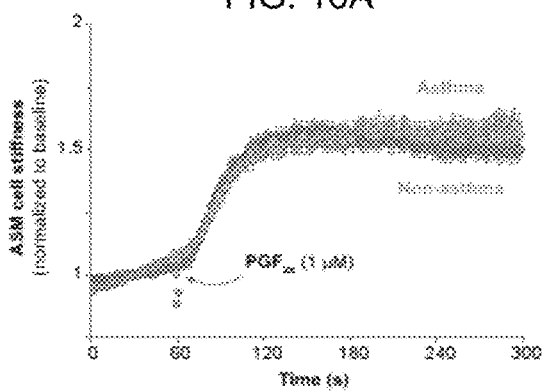
Figure 16D:
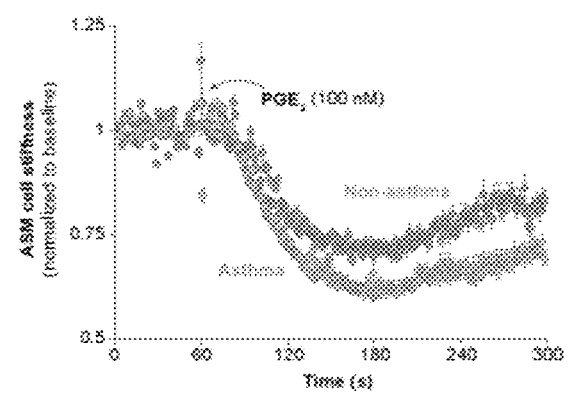
Figure 16E:
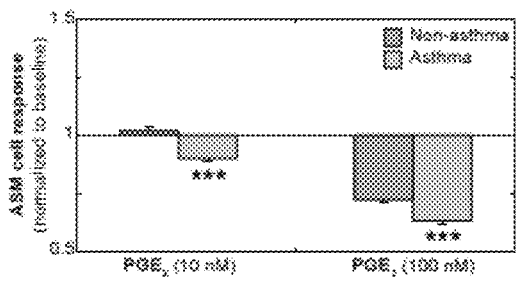
Figure 16F:
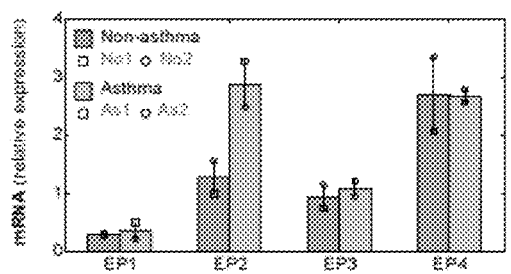
Figure 16G:
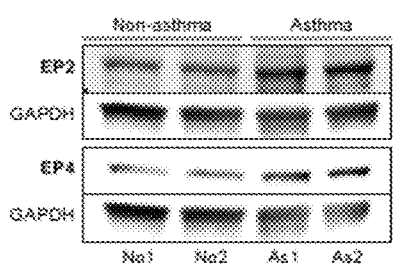
Figure 16H:
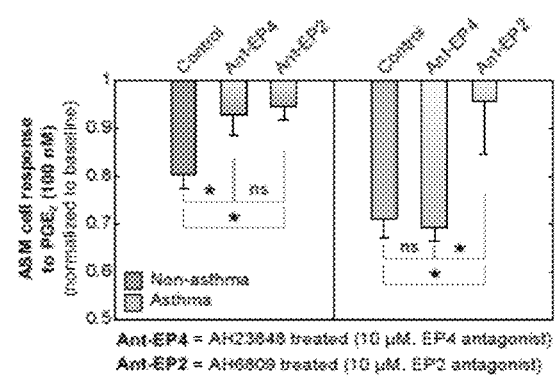
Figure 20A:
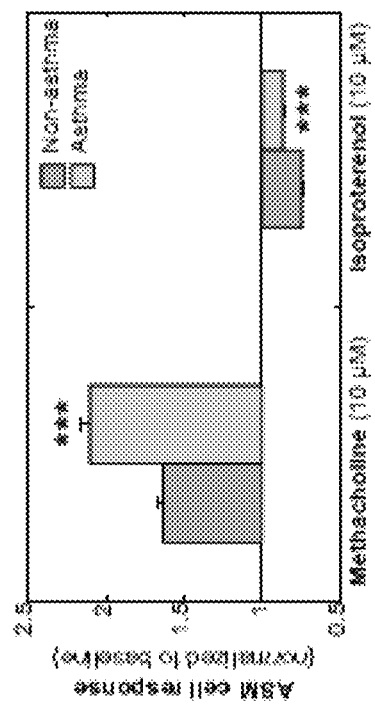
FIGS. 20A-20C are a series of graphical representations depicting data relating to asthmatic and non-asthmatic smooth-muscle-cell response in embodiments of the invention.
Figure 20C:
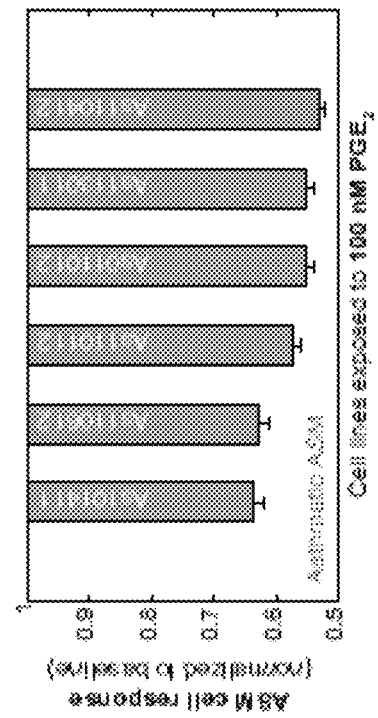
Figure 20B:
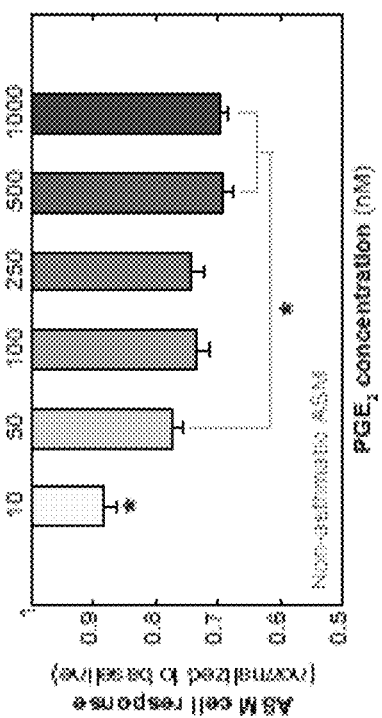

For these experiments, primary ASM cells derived from the lungs of asthmatic and non-asthmatic donors were used. To assess differences between these two groups of ASM cells in response to various agonists of interest, the inventors first tested their response to methacholine, a synthetic muscarinic receptor agonist used to diagnose bronchial hyperreactivity. In agreement with a study showing asthmatic and non-asthmatic ASM cells possessing different mechanophenotypes, the inventors observed stronger contraction in asthmatic ASM cells (FIG. 16A). Similarly, the beta-adrenergic agonist isoproterenol yielded less relaxation in asthmatic ASM cells (FIG. 20A). Together, these results indicated hyperresponsive behavior in the asthmatic ASM cells. Interestingly, however, the response of these cells to infranatant samples from epithelial cells treated with different pressure durations showed contractility at similar levels (FIG. 13C), with slightly weaker response in the asthmatic ASM group. To shed light on these different responses, next the inventors tested ASM response to different eicosanoids. Surprisingly, the spasmogen prostanoid $PGF_{2\alpha}$ did not yield a difference in response between asthmatic and non-asthmatic ASM cells (FIG. 16C). It has been reported that $PGE_2$ causes bronchial dilation in non-asthmatic human subjects, while it can cause either bronchial dilation or constriction in asthmatic patients. It was therefore analyzed the effect of $PGE_2$ on asthmatic and non-asthmatic ASM cells. $PGE_2$ consistently caused ASM relaxation for different doses (FIG. 20B) and for different patient samples tested (FIG. 20C). Interestingly, asthmatic ASM cells relaxed more in response to $PGE_2$ (FIGS. 16D-E). This has been hypothesized to be due to different expression levels of various EP receptors. Indeed, expression of PTGER1-4 mRNA (FIG. 16F) and protein expression analysis (FIG. 16G), and pharmacological inhibition of specific EP receptors (FIG. 16H) revealed that the different response is primarily due to different expression levels of the EP2 receptor. Together, these results revealed distinct mechanophenotypes, where asthmatic ASM cells showed hyperresponsiveness, while relaxing more in response to $PGE_2$. To better understand the effect of such different ASM mechanophenotypes, the inventors therefore developed the model depicted in FIG. 17A, and simulated bronchospasm dynamics for different ASM contractility levels.

Model and Experiments Indicate Feedback Leads to Bronchospasm Memory Effect.

Figure 14B:
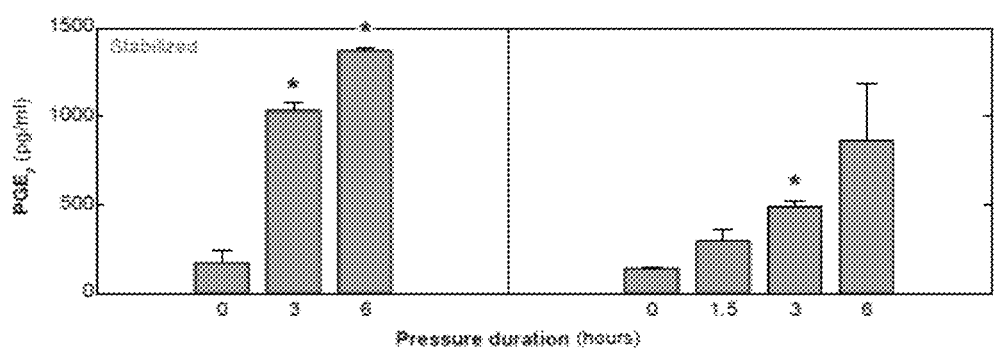

The proposed model (FIG. 17A) depicts an external stimulus such as histamine due to an allergic reaction or acetylcholine due to a nervous system response that leads to ASM contraction, which applies compressive stress on the epithelium. In response to the compressive stress, epithelial cells produce eicosanoids that in turn cause ASM contraction. If the contraction of the ASM is strong enough, the eicosanoids produced by the epithelium will keep the ASM contracted, even when the external stimulus disappears. This is the memory effect predicted by our theoretical model (FIG. 17B). For severe bronchospasm, the compressive stress on epithelial cells can reach levels as high as 30 cmH$_2$O. Due to the hypercontractility of asthmatic ASM to external stimuli, severe bronchospasm would be expected to occur more likely in asthmatic airways. Measurements using the lung chip show that for these levels of compressive stress, epithelial cell products indeed cause maximum contraction in ASM cells (FIG. 17C). Application of compressive stress on the epithelial layer in the lung chips led to strong contraction in the ASM layer (n=3 lung-chips). Turning off the pressure did not relax the baseline, and treating the ASM cells with methacholine only slightly increased ASM contraction. Interestingly, treatment of the ASM cells with PGE$_2$ did not lead to relaxation, indicating that the effect of pressure extends beyond the duration where compressive stress is applied. Reapplying the compressive stress did not increase ASM contraction further either, consistent with our claim that the ASM cells reached maximum contraction levels. This result supports the argument that coupling between ASM contraction and epithelial signaling could be a significant contributor to extended episodes of bronchospasm in asthmatic airways. The question that remains is then whether there are mechanisms present that allow the airways to relax after becoming locked in a bronchospasm. The theoretical model predicts that the airways can relax from their bronchospasm state if the component of the epithelial signaling responsible for ASM relaxation becomes stronger (FIG. 17B). As evident from FIG. 16B, longer durations (6h vs. 3h) of compressive stress indeed lead to less contraction in ASM cells. This is consistent with the increasing PGE$_2$ levels over time (FIG. 14B). Furthermore, when ASM cells were exposed to epithelial infranatants overnight, it was observed a reduction of the baseline stiffness (muscle tone) of the cells (FIG. 17D). This indicates that as a result of compressive stress, epithelial cells release products that work over longer time scales, which lead to relaxation of ASM cells.

Discussions

In this study, using primary human cells, we show that compressive stress on airway epithelial cells leads to strong contraction in ASM cells, suggesting positive feedback during bronchospasm. The quantitative results indicate that for severe bronchospasm this positive feedback could be strong enough to lead to irreversibility, i.e., a sustained constricted state even after the removal of external stimuli.

A striking aspect of the results is how rapidly ASM cells are able to respond following the application of mechanical stress on epithelial cells. Similar rapid responses have been observed in recent studies using ex vivo lung-tissue slices from rats, where local injury to a single epithelial cell triggered an instantaneous Ca$^{2+}$ wave throughout the epithelium and induced ASM contraction within several seconds that lasted for tens of seconds. It was observed that epithelial injury triggered the release of ATP, and airway contraction was completely blocked by selective inhibition of COX2. While in these studies ASM contraction was triggered by injury to the epithelium, mechanically stimulating the epithelium can be sufficient to obtain similar results. Earlier studies using guinea pig trachea in vitro showed that gentle mechanical irritation of the mucosal surface triggers the release of PGE$_2$ and PGF$_{2\alpha}$, and that the effect of the mechanical stimulus can be blocked by cyclooxygenase inhibition. Prostaglandin release was also induced by contracting the trachea with histamine or acetylcholine. Similarly, application of a tensile stress on guinea pig trachea in vitro triggered airway contraction. This stretch-induced contraction was maintained only in tissues with an intact epithelium, and was absent in tissues with the epithelium removed, or when prostaglandin synthesis was inhibited. It is important to note that, using our microphysiological airway model, a similar sustained contraction state of ASM cells in the presence of an epithelium following mechanical stress was observed. Despite a difference in the type of mechanical stimuli and the experimental models used, these previous studies show parallels to these results regarding the role of cyclooxygenase and the mainly contractile response of ASM to epithelial factors released through mechanical stress.

How mechanical stress exactly regulates the release or synthesis of epithelium-derived spasmogens is, however, not clear. The results indicate that YAP regulates COX2 expression. Furthermore, pharmacological inhibition of YAP blocks ASM contraction triggered by mechanical-stress induced epithelial-spasmogen release. Therefore, YAP-associated mechanosensing is a likely mechanism of how ASM contraction is regulated via mechanical stress on the epithelium. However, this transcriptional regulation is expected to work only at longer time scales. The results indicate that compressive stress on the epithelium can lead to ASM contraction within much shorter time scales of a few minutes. Various mechanosensitive ion channels are known to be expressed in epithelial cells that could initiate a rapid response to mechanical stress, such as transient receptor potential channel (TRP), epithelial sodium channel, cystic fibrosis transmembrane conductance regulator, and Piezo1. In airway epithelial cells mechanical transduction through TRP and Rho signaling can mediate direct ATP release through the large transmembrane channel Pannexin1, which also allows efflux of other small molecules including prostaglandins. In other cell types, mechanical loading can lead to Ca$^{2+}$ dependent rapid vesicular release of ATP, which can then mediate prostaglandin release through autocrine signaling. Therefore, besides epithelial injury, spasmogen release due to mechanical activation of ion channels could be a potential mechanism that triggers rapid ASM contraction in response to compressive stress on the epithelium. Taken together, this points to a need for more thorough mechanistic studies of epithelium-ASM interactions at different time scales. The inventors believe our reductionist microphysiological airway model provides the means for such investigations in the future.

It is interesting to note that removal or absence of the epithelium in general is expected to lead to hypersensitivity in the response to spasmogens. Several studies using lung-slice models suggest that the airway epithelium modulates ASM tone through the release of relaxants, so that contraction is reduced in response to spasmogens such as acetylcholine, histamine, or PGF$_{2\alpha}$. However, in contrast to the acute effects of mechanical stimuli, this relaxant release likely occurs continuously on a basal level and is not dependent on the activation of specific epithelial receptors. Furthermore, there are also questions regarding the suitability of these systems for mechanistic studies. An advantage of lung slices is that they provide a physiologically more relevant system as they are derived from actual tissue and hence contain various other cell types besides epithelial and ASM cells, such as nerve cells, immune cells, fibroblasts, and blood vessels. However, this also makes the model less tractable and complicates interpretation of the results on a mechanistic level. The mechanisms behind the relaxing effect of the epithelium on ASM tone is not clear as it seems to involve crosstalk with neural pathways. For example, it was reported that the relaxing effect of the epithelium on ASM contraction was lost following denervation in auto-transplanted canine airways. $PGE_2$, an epithelial factor that in general causes ASM relaxation in humans, was found to cause bronchial contraction in conscious mice, and bronchial dilations in anesthetized mice or in denervated tissues. This suggests that the continuous modulation of ASM tone through epithelial factors might require neural stimulation, in contrast to the simple epithelium-ASM interaction through mechanical stress.

Figures 21A, 21B:
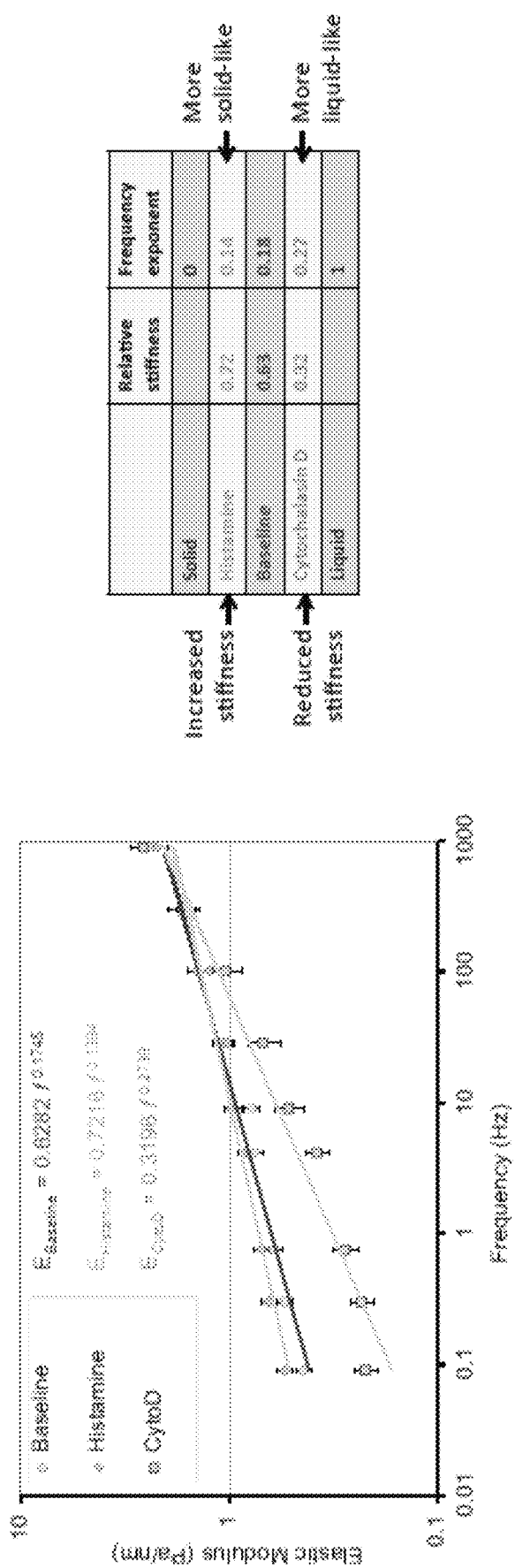
FIGS. 21A-21B are a series of graphical and tabular representations depicting data relating to cell rheology measurements in embodiments of the invention.

One of the most important aspects of our platform is that it allows mechanistic studies not possible with in vivo or existing in vitro experimental models, and that the inventors can perform quantitative analysis with high precision in a highly controlled environment (including quantitative cell-rheology measurements; FIG. 21). As discussed, some of the effects of the epithelium on ASM and the response of epithelial cells to various types of mechanical stress have been reported before. However, the potential influence of these interactions on bronchospasm dynamics has not been investigated mainly due to a lack of quantitative methods. The platform of the invention circumvented these limitations and revealed important mechanisms with implications to in vivo processes. Notably, the results provided evidence that hypercontractility of ASM, a hallmark of asthma, may lead to irreversible bronchospasm due to mechanical feedback between epithelium and ASM. While caution should be used when drawing conclusions through such a reductionist approach, understanding of isolated contributors to the pathological state of asthma is essential to construct a complete model that can adequately describe this complex multi-scale condition, so that better therapeutic approaches can be developed.

Material and Methods

Bronchi-on-a-Chip Fabrication.

The upper and lower layer of the microfluidic device were fabricated using standard soft lithography techniques by casting a flexible and optically transparent polydimethylsiloxane (PDMS) polymer on a mold and cross-linking at 80° C. for 2 hours. The mold was fabricated using optical lithography with an epoxy-based negative photoresist (SU8) that yields thick and robust structures. The two PDMS layers each had compartments with 5 mm width, 20 mm length, and 300 μm height, and around 100 support pillars with 200 μm diameter distributed across the compartments. The two compartments were separated by an optically-clear polycarbonate membrane (Sterlitech) with 5 μm diameter holes, allowing cells on both sides of the membranes to chemically interact. To construct the complete chip, first a PDMS layer and the polycarbonate membrane were exposed to an oxygen plasma (30 W, 700 mTorr, 30 sec) to chemically activate their surfaces. Immediately after the plasma treatment, the PDMS surface was silanized using 5 μl of an APTES solution (1% 3-aminopropyltriethoxysilane in water) and the polycarbonate membrane was allowed to bond to it. After 2 hours of bonding at room temperature, the process was repeated to bond the second PDMS compartment to the other side of the polycarbonate membrane. The APTES silanization allowed a strong permanent bond between the layers that we were not able to pull apart manually. The device was further bonded to a glass coverslip for support using an oxygen plasma. After the chip was sterilized under intense UV light overnight, the two compartments were coated with collagen type I and subsequently seeded with primary normal human bronchial epithelial (NHBE) cells on the top compartment. Following the maturation of the NHBE cells in an ALI, primary HASM cells were seeded on the bottom compartment.

Cell Culture.

Primary human epithelial and smooth muscle cells were harvested from the proximal airways (first through third order bronchi) of donor lungs unsuitable for transplantation (Table I) in accordance with the Institutional Review Boards at the University of Pennsylvania. Primary normal human bronchial epithelial (NHBE) cells were grown in collagen-coated flasks (GIBCO) using serum-free BEGM Bronchial Epithelial Cell Growth Medium™ with BulletKit™ Supplements (Lonza) and subsequently trypsinized and seeded onto porous polycarbonate membranes (either inside microfluidic devices or on transwell inserts) at 100,000 cells/$cm^2$. The polycarbonate membranes were coated with collagen type I (30 μg/ml; GIBCO) at 37° C. for 18 h before cell seeding. After NHBE cells reached confluence (within 3-5 days), the apical medium was removed and the basal medium was replaced with differentiation medium (PneumaCult-ALI™ Medium and Supplements, StemCell Technologies). The NHBE cells were maintained at the ALI for 2-3 weeks, until they differentiated into a pseudostratified layer. Excess mucus on the air side was washed away with warm PBS weekly. After NHBE differentiation in the microfluidic chips, primary HASM cells were seeded into the bottom compartment. Approximately 18 h before the live-cell micromechanical experiments using MTC, the culture medium of HASM cells was changed to serum-free minimal media (1:1 vol/vol mixture of DMEM Dulbecco's modified Eagle's medium and Ham's F-12 medium, supplemented with insulin (10 mg/ml), transferrin (5.5 mg/ml), and selenium (6.7 mg/ml)), and cells were maintained at 37° C. in humidified air containing 5% $CO_2$. The overnight media was then washed and replaced with fresh minimal media before the experiments. This minimal media procedure was applied to NHBE cells as well before compressive-stress application. For experiments involving Celecoxib or Verteporfin (Sigma Aldrich), NHBE cells were pre-treated with the drugs before the second washing step, as the presence of Celecoxib in the infranatant affected HASM mechanics (FIGS. 19A-B), and Verteporfin in the infranatant would have phototoxic effects on HASM cells during the live-cell micromechanical measurements. Since Verteporfin is a photosensitizer, treatment of NHBE cells was always performed in the dark.

TABLE I

| Donor | Age | Gender | Race and Ethnicity | Cause of Death |
|---|---|---|---|---|
| Non-asthma HASM | | | | |
| No50612 | 55 | F | Caucasian | CNS Tumor |
| No090712 | 22 | F | Caucasian | Seizure |
| No101412 | 11 | M | Caucasian | Head trauma |
| No41213 | 49 | M | Caucasian | CVA, Chewing tobacco 20 yrs |
| Asthma HASM | | | | |

TABLE I-continued

| Donor | Age | Gender | Race and Ethnicity | Cause of Death |
|---|---|---|---|---|
| As101411 | 26 | F | Black | Anoxia |
| As110612 | 38 | M | Caucasian | Anoxia |
| As110112 | 22 | M | Black | Anoxia |
| As011012 | 18 | F | Caucasian | Head trauma |
| As113011 | 25 | F | Caucasian | Anoxia |
| As110412 | 13 | F | Caucasian | Anoxia |
| As112113 | 44 | M | Hispanic | Anoxia |

Compressive Stress Application.

To expose NHBE cells in an ALI to apical compressive stress in the microfluidic device, we connected the top compartment to a custom-built pressure regulator that circulates the ambient air through a sterile 0.2 µm pore filter and compresses it to a level of 30 $cmH_2O$ pressure, while the basal side of the cells remained at atmospheric pressure. The pressure regulator (FIG. 18D) consists of a micro pump (AP-2P02A, SmartProducts) and a 30 $cmH_2O$ pressure release valve (SmartProducts), and is powered by high-temperature compatible lithium batteries. To apply compressive stress to NHBE cells on the apical side in transwell inserts, the inventors built a custom transcellular pressure setup consisting of a 6-well plate with rubber plugs that have access ports connected first to sterile filters and then in parallel to the pressure regulator (FIG. 13A, FIG. 18D). To reduce evaporation during long pressure-application experiments, the wells are covered by a flexible and breathable PDMS cover. Before each experiment, the rubber plugs were autoclaved and the PDMS covers were sterilized with intense overnight UV exposure.

HASM Stiffness Measurements.

Magnetic twisting cytometry with optical detection was used to quantitatively assess dynamic changes in cell stiffness as an indicator of single-cell contraction or relaxation of HASM cells, as previously described. In brief, ferrimagnetic microbeads (4.5 µm in diameter) coated with synthetic Arg-Gly-Asp (RGD) containing peptide (American Peptide Company) bound to the cytoskeleton through cell surface integrin receptors were magnetized horizontally. Subsequently, a vertically aligned homogeneous magnetic field varying sinusoidally in time applied an oscillatory torque, leading to both a rotation and a pivoting displacement of the bead (FIG. 18B). Measurements were performed at a single frequency of 0.75 Hz or oscillatory frequencies between $10^{-1}$ and $10^3$ Hz for cell rheology measurements (FIG. 21). Lateral bead displacements in response to the resulting oscillatory torque were detected optically (in spatial resolution of ~5 nm), and the ratio of specific torque to bead displacement was computed as the cell stiffness in units of Pascals (Pa) per nanometer. For drug-induced single-cell contraction or relaxation, changes in HASM stiffness were measured in real-time for the duration of 300 seconds. For each individual cell, the baseline stiffness was measured for the first 60 seconds, and after drug addition, the stiffness was measured continuously for the next 240 seconds.

Lentiviral Transduction.

Lentiviral transduction particles (Sigma Aldrich) containing empty (TRC1) or YAP shRNA (TRCN0000107266) lentiviral constructs were used as the Control or shYAP virus. Primary NHBE cells were transduced with equal titers of concentrated virus in complete growth media supplemented with 1 µg/ml polybrene (Sigma Aldrich) for 24 hours. Following transduction, cells were given 24 hours to recover before selection in 0.5 µg/ml puromycin (Sigma Aldrich) for a minimum of 6 days. Minimum effective puromycin concentration was determined using kill curves of untransduced cells (data not shown).

Immunoblotting.

Primary NHBE cells were lysed on ice with a cell scraper and radioimmunoprecipitation assay lysis buffer (Pierce) supplemented with protease inhibitor tablets (Roche) and a phosphatase inhibitor cocktail (Pierce). Extracts were incubated for 45 minutes for complete lysis and centrifuged at 10,000 RPM for 10 minutes at 4° C. to pellet cell debris. Supernatant protein concentrations were quantified using a BCA Protein Assay kit (Pierce) and a spectrophotometric plate reader (BioTek). Most protein lysates were separated by running 30-100 µg of lysate on 10% Bis-Tris NuPage™ gels (Invitrogen) and subsequently transferred to 0.2 µm pore polyvinylidene fluoride (PVDF) membranes (BioRad). Primary antibody (listed in table below) incubations were according to manufacturer's recommendations in 0.1% Tween TBS supplemented with 5% non-fat dry milk or BSA, as recommended. Immunoreactive bands were visualized using the appropriate horseradish peroxidase-conjugated anti-IgG antibodies (Pierce). Bands were detected using enhanced chemiluminescence or prime detection reagent (GE Healthcare) whenever appropriate.

TABLE II

| Target protein | Antibody | Target protein | Antibody |
|---|---|---|---|
| YAP | Cell Signaling 4912 | EP1 (PTGER1) | Santa Cruz sc-20674 (H-60) |
| COX1 | Cell Signaling 4841 | EP2 (PTGER2) | R&D Systems mab6656 (C-607077) |
| COX2 | Cell Signaling 12282 (D5H5) | EP3 (PTGER3) | Santa Cruz sc-57105 (5F5) |
| Beta-actin | Abcam ab8227 | EP4 (PTGER4) | Santa Cruz sc-55596 (C-4) |
| | | GAPDH | Cell Signaling 5174 (D16H11) |

Gene Expression Analysis.

For these studies, cDNA was generated using random hexamer primers and SuperScript II Reverse Transcriptase™ (Applied Biosystems). Real-time PCR was performed using TaqMan™ Universal PCR Master Mix, fluorogenic probes, and oligonucleotide primers. TaqMan™ assays were repeated in triplicate samples for each of the target genes. The $2^{-\Delta\Delta Ct}$ method was used to calculate the relative fold change (RFC) of transcripts normalized to a house-keeping gene (GAPDH). Primer-probe sets for the analyzed genes are listed in the table below.

TABLE III

| Target gene | TaqMan™ primer-probe set | Target gene | TaqMan™ primer-probe set |
|---|---|---|---|
| PTGS1 (COX1) | Hs00377726 | PTGER1 (EP1) | Hs00168752 |
| PTGS2 (COX2) | Hs00153133 | PTGER2 (EP2) | Hs00168754 |
| YAP1 | Hs00902712 | PTGER3 (EP3) | Hs00168755 |

TABLE III-continued

| Target gene | TaqMan™ primer-probe set | Target gene | TaqMan™ primer-probe set |
|---|---|---|---|
| CTGF | Hs01026927 | PTGER4 (EP4) | Hs00168761 |
| ANKRD1 | Hs00923599 | GAPDH | Hs02758991 |

Prostaglandin Detection.

Media from the basal compartments (infranatant) were collected from control samples or after application of 30 cmH$_2$O compressive stress on NHBE cells, and were assayed for the presence of PGE$_2$ using a commercial EIA kit (DetectX™ Prostaglandin E2 High Sensitivity Immunoassay Kit, Arbor Assays, Ann Arbor, Mich.) following the manufacturer's instructions. The absorbance in the samples was measured at 450 nm with a microplate reader (Molecular Devices, Sunnyvale, Calif.). The concentration of PGE$_2$ was calculated from a standard curve derived using recombinant proteins. All samples were assayed in triplicate.

Statistics.

Pairwise comparisons of normalized data was performed using the t-test (FIG. 15A, FIG. 16E), and of non-normalized data using the Wilcoxon rank-sum test (FIG. 6C-D), with significance based on *p<0.05, p<0.01, and *p<0.001. For exploratory screening with small sample sizes (n=3) and involving multiple comparisons, False Discovery Rate (FDR) was controlled using the Benjamini-Hochberg procedure at a level of FDR=10% (FIG. 3A-B, FIG. 4B-D). For confirmatory analysis involving multiple comparisons, the Family Wise Error Rate (FWER) was controlled using one-way ANOVA followed by Bonferroni's post-hoc test at a level of FWER=5% (FIG. 13C-D, FIG. 16B,H). Significance based on FDR and FWER took into account any additional comparisons performed in the supplementary data. All statistical tests performed were two-tailed.

Airway ODE Model.

The airway ODE model described below was solved with Oscill8™ Dynamical Systems Toolset and further processed with Matlab™.

Figure 17A:
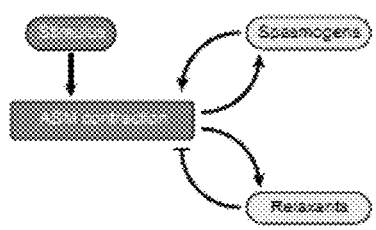
FIGS. 17A-17D are a series of schematic and graphical representations relating to an airway feedback model.
Figure 17B:
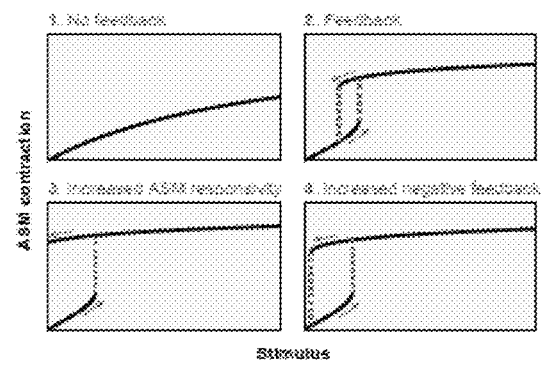
Figure 17C:
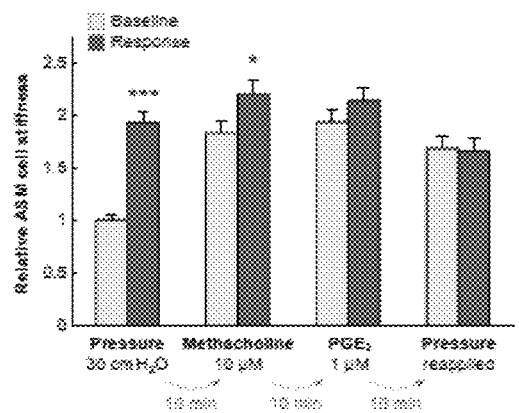
Figure 17D:
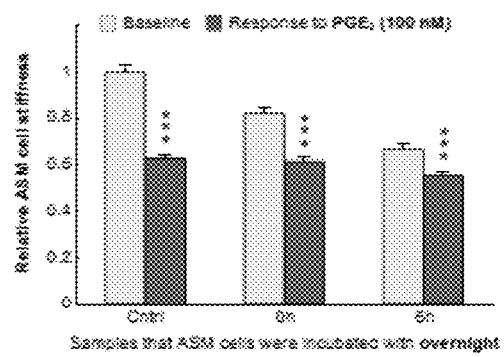

To model the system in FIG. 17A the HASM contraction level was represented by C, the external stimulus level by S, and the levels for the epithelium-derived spasmogens and relaxants as $E_1$ and $E_2$, respectively. Basal expression rates for the eicosanoids are ignored for simplicity, as simulations showed that they do not affect the general results of the model. The system then can be represented by the following set of ODE equations:

$$\frac{dE_1}{dt} = \frac{E_{1_{max}}}{\tau_1} h_1(C) - \frac{E_1}{\tau_1} \quad \text{(I)}$$

$$\frac{dE_2}{dt} = \frac{E_{2_{max}}}{\tau_2} h_2(C) - \frac{E_2}{\tau_2} \quad \text{(II)}$$

$$\frac{dC}{dt} = \frac{C_{max}}{\tau_C} h(S, E_1, E_2) - \frac{C}{\tau_C} \quad \text{(III)}$$

Expression rates of spasmogens and relaxants are represented by $\tau_{1,2}$ and the time scale for contraction by $\tau_C$, where $\tau_{1,2} \gg \tau_C$. Maximum expression levels are $E_{1,2_{max}}$ and maximum HASM contraction is $C_{max}$. Positive feedback is assumed an order-of-magnitude stronger than negative feedback, so that $E_{1_{max}} \gg E_{2_{max}}$. Dependence of spasmogen and relaxant production on contraction, and dependence of contraction on stimuli are approximated with Hill functions:

$$h_1(C) = \frac{(C/K_{C1})^m}{1+(C/K_{C1})^m}, h_2(C) = \frac{(C/K_{C2})^n}{1+(C/K_{C2})^n} \quad \text{(IV)}$$

$$h(S, E_1, E_2) = \frac{(S/K_S)^n + (E_1/K_{E1})^n}{1+(S/K_S)^n + (E_1/K_{E1})^n + (E_2/K_{E2})^n} \quad \text{(V)}$$

The parameters are arbitrarily chosen to observe effects of the feedback within the stimulus range of $0 \leq S \leq 1$. However, we note that the conditions of observing a memory effect and general conclusions of the model are independent of the particulars of the model or the values of the parameters. The inventors set $\tau_C = 1$ and $\tau_1 = \tau_2 = 10$, $K_S = K_{E1} = K_{E2} = 1$ and $K_{C1} = K_{C2} = 2$. Based on typical response curves (see, e.g., (49, 53, 54)) we can approximate m=3 and n=1.

Results of the model are shown in FIG. 17B, where the x-axis range is set as $0 \leq S \leq 1$, and the y-axis range is set as $0 \leq C \leq C_{max}$ C=1. For FIG. 6B(2), we set $E_{1_{max}} = 60$, and $E_{2_{max}} = 6$. For FIG. 6B(3), we increase HASM contractility by 5% $C_{max} = 1.05$, and then for FIG. 6B(4) we further increase the negative-feedback component ($E_{2_{max}}$) by 30%.

Figure Captions

FIG. 12 illustrates that the lung-chip results indicate positive feedback between smooth-muscle contraction and compressive stress on epithelium. (A) Contraction of airway smooth muscle leads to mechanical stress in airway epithelium, which may result in paracrine signaling. (B) To quantitatively analyze this interaction, a model system using a lung-chip platform was developed. Regulated air pressure applies compressive stress at physiological levels on human airway epithelial cells. Resulting changes in human airway smooth-muscle mechanical properties are quantitatively measured using optical magnetic-twisting cytometry. (C) Human airway smooth-muscle layer inside lung-chip, with RGD-coated magnetic beads that bind to cell surface integrin receptors, hence allow probing of the actin cytoskeleton. (D) 30 cmH$_2$O compressive stress applied after t=60 seconds on the epithelial-cell layer leads to smooth-muscle contraction, whereby cell stiffness changes more than twofold within two minutes (n~300 for three different chips tested, error bars represent SEM).

FIG. 13 illustrates that feedback manifests over longer durations mainly through eicosanoid production. (A) Setup that allows analysis of the effects of compressive stress on airway epithelial cells in a more controlled environment and with more cell numbers. The setup is based on a six-well platform with pseudostratified normal human airway epithelial cells in an air-liquid interface. (B) Infranatant from compressive-stress-treated epithelial cells causes strong contraction in ASM cells (Control=untreated medium). (C) COX2 inhibitor Celecoxib suppresses the effects of compressive stress on epithelial cells, as ASM cell contraction in response to 0h and 3h-pressure epithelial samples are at similar levels. (Asterisks indicate significance to all other conditions.) (D) Response of drug-treated ASM cells to 3h-pressure epithelial infranatant. The drugs antagonize different eicosanoid receptors that are involved in contraction initiation. AL=AL8810, PGF$_{2\alpha}$ receptor (FP) antagonist. ICI=ICI192605, thromboxane receptor (TP) antagonist. Zaf=Zafirlukast, CysLT1 receptor antagonist. (Asterisks indicate significance to control. Differences between different drug treatments are not significant.) Error bars represent SEM, n>100.

FIG. 14 illustrates that eicosanoid production is regulated by modulation of COX by compressive stress. (A) Compressive stress differentially regulates COX1 and COX2 mRNA expression in airway epithelial cells. (B) $PGE_2$ content of epithelial infranatant. (Asterisks indicate significance to control. Controls are samples with no pressure applied. Before the pressure experiments, overnight media is washed away, and replaced with fresh media. Stabilized=overnight media remains in the setup during the pressure experiments.) Error bars represent SEM, n=3.

FIG. 15 illustrates that compressive stress is relayed to COX through the mechanosensor YAP. (A) ASM cell contraction in response to infranatant from epithelial cells exposed to compressive stress and/or treated with the YAP inhibitor Verteporfin. (B) Effects of Celecoxib and Verteporfin on COX1 and COX2 mRNA expression in airway epithelial cells. (C) $PGE_2$ content of epithelial infranatant in response to Celecoxib and Verteporfin treatment. (D) Expression of YAP1 mRNA and its target CTGF in epithelial cells. Controls are samples with no pressure applied. (E) Western blots of COX1 and COX2 expression in epithelial cells transduced with shYAP or a control virus. Error bars represent SEM, n>100 (A), n=3 (B-D).

FIG. 16 illustrates that smooth-muscle cells have different mechanophenotypes. (A) Stiffness change of non-asthmatic and asthmatic ASM cells in response to methacholine. (B) Response of normal and asthmatic ASM cells to infranatant samples from epithelial cells treated with different pressure durations. (Asterisks indicate significance to all other conditions.) (C-D) Stiffness change of ASM cells in response to $PGF_{2\alpha}$ (C) and $PGE_2$ (D). (E) ASM cell response to low and high doses of $PGE_2$. (F-G) Comparison of mRNA (F) and protein expression (G) of eicosanoid receptors for non-asthmatic and asthmatic ASM cells (cell lines from two different patients each). (H) Response to $PGE_2$ of non-asthmatic and asthmatic ASM cells treated with EP4 and EP2 antagonists. Error bars represent SEM, n>100.

FIG. 17 illustrates a model and experiments that indicate feedback leads to bronchospasm memory effect. (A) Schematic of airway feedback model: ASM contraction is driven by an external stimulus, such as histamine due to an allergic reaction or acetylcholine due to a nervous system response. Once ASM contract and apply compressive stress on the epithelium, a positive and negative feedback through eicosanoid production is activated. (B) Predictions of an ODE model (see supplements) describing the system in (A). The vertical axes range from 0 to maximum ASM contraction. Without feedback, ASM contraction levels increase smoothly in response to stimulus levels (1). When positive feedback is stronger than negative feedback, the response displays sensitivity amplification, and can display hysteresis (2). When the ASM possess a more contractile phenotype, the eicosanoids produced will keep the ASM contracted even when the external stimulus disappears. This irreversibility leads to a memory effect during bronchospasm (3). ASM can relax from their irreversible state if effects of negative feedback become stronger over time (4). (C) Compressive stress on epithelial cells saturates contraction of ASM cells in the lung-chip platform, indicating that smooth muscle-epithelium feedback can lead to irreversibility during bronchospasm. First a 30 $cmH_2O$ compressive stress is applied on epithelial cells, leading to strong contraction in ASM cells. After pressure is turned off, 10 μM methacholine is introduced into the chip, followed by 1 μM $PGE_2$, and finally 30 $cmH_2O$ compressive stress is reapplied (n~300 for three different chips tested, error bars represent SEM). (D) Epithelial products lead to ASM cell relaxation over extended time periods. ASM cells were incubated with epithelial infranatant samples overnight (18 hours) and then exposed to $PGE_2$. Error bars represent SEM, n>100.

FIG. 18 illustrates a lung-chip and optical magnetic twisting cytometry. (A) Photographs of lung-chip platform and optical magnetic twisting cytometry setup. (B) Optical magnetic twisting cytometry (OMTC): RGD-coated ferri-magnetic beads bind to cell-surface integrin receptors, hence allow direct probing of the actin cytoskeleton. First, the magnetizing coils (shown in (A)) impart a strong magnetic pulse and thereby magnetize the beads so that their magnetic moments point in the horizontal direction. Then, using the twisting coil (shown in (A)), a weaker magnetic field is oscillated in the vertical direction, leading to a twisting motion of the attached beads. An optical microscope automatically tracks the horizontal motion of the beads, which is then converted into data describing the physical properties of the probed actin cytoskeleton. (C) Human airway smooth-muscle layer inside well, with RGD-coated magnetic beads attached to cell surfaces. (D) Photograph of setup that allows analysis of the effects of compressive stress on airway epithelial cells with more cell numbers. (E) Protocol for quantifying effects of infranatant collected from airway epithelial cells on ASM cell mechanics.

FIG. 19 illustrates stabilized vs pre-treated samples. (Stabilized=Overnight media with or without drugs remains in the setup during the pressure experiments. Pre-treated=Before the pressure experiments, overnight media with or without drugs is washed away, and replaced with fresh media without drugs.) (A) Pharmacological COX2 inhibition leads to reduced COX2 mRNA expression levels, consistent with positive feedback between $PGE_2$ and COX2. (B) Expression of YAP1 mRNA and associated targets CTGF and ANKRD1 in pre-treated samples (i.e., Celecoxib and Verteporfin are not present in the media during the pressure experiments). (C) Stabilized infranatant from epithelial cells treated with Celecoxib causes contraction. The presence of Celecoxib in the infranatant appears to significantly contribute to the contraction. (D) For both stabilized and pre-treated epithelial samples, Celecoxib suppresses the effects of compressive stress, as ASM cell contraction in response to 0h and 3h-pressure samples are at similar levels. (Asterisks indicate significance to all other conditions, unless otherwise highlighted.) (Asterisks indicate significance to control. Controls are samples with no pressure applied.) Error bars represent SEM, n=3 (A-B), n>100 (C-D).

FIG. 20 illustrates asthmatic and non-asthmatic smooth-muscle-cell response. (A) Asthmatic ASM display hyper-contractility in response to methacholine, while the beta-adrenergic agonist isoproterenol yields less relaxation in asthmatic ASM cells. (B) $PGE_2$ dose response of normal airway smooth-muscle (ASM) cells. (Asterisks indicate significance to all other conditions, unless otherwise highlighted.) (C) Response of airway ASM cells from six different asthma patients to 100 nM $PGE_2$. Error bars represent SEM, n>100.

FIG. 21 illustrates cell rheology measurements using the lung-chip platform. Frequency-domain OMTC measurements on lung-chip treated with agents causing relaxation (cytochalasin D) or contraction (histamine). Histamine increases ASM cell stiffness, and it becomes more difficult (slower) for the cells to relax stress. Inhibiting actin polymerization (cytochalasin D), on the other hand, reduces ASM cell stiffness, and it becomes easier (faster) for the cells to relax stress.

Although the invention has been described with reference to the above example, it will be understood that modifications and variations are encompassed within the spirit and scope of the invention. Accordingly, the invention is limited only by the following claims.

What is claimed is:

1. A microphysiology device for mimicking a biological tissue, the device comprising:
a body having a top compartment having a first fluid channel, and a bottom compartment having a second fluid channel, the top and bottom compartments being separated by a porous membrane that is partially or entirely optically transparent, wherein the porous membrane comprises at least one agent adapted to support adherence of a living cell,
wherein the porous membrane comprises pores fluidly connecting the first and second fluid channels, the pores dimensioned between about 0.2 microns and 10 microns, and the first and second fluid channels having a width between about 1 and 5 mm, a length between about 5 and 20 mm, and a height between about 50 and 500 µm, wherein support pillars with a diameter between about 50 and 250 µm are distributed within the first and second fluid channels, and wherein the length of the first fluid channel is disposed perpendicular to the length of the second fluid channel.

2. The device of claim 1, wherein the biological tissue is a functional organ.

3. The device of claim 2, wherein the organ is mammalian.

4. The device of claim 3, wherein the mammal is human.

5. The device of claim 1, further comprising:
at least two access ports through the body,
wherein the first access port provides a fluid path through the body into the top compartment, and the second access port provides a fluid path though the body into the bottom compartment, and
wherein a pressure applied to the top compartment through the first access port introduces a compressive stress gradient on a cell adhered to the membrane.

6. The device of claim 5, wherein the first access port is fluidly coupled to a fluid supply.

7. The device of claim 6, wherein the fluid supply is gas.

8. The device of claim 1, further comprising at least one access hole through the body providing access to the bottom compartment, top compartment, or both.

9. The device of claim 1, wherein the bottom compartment is coated with at least one molecule that supports adherence of a living cell.

10. The device of claim 9, wherein the agent is selected from the group consisting of polypeptide, entactin, glycoprotein, collagen, fibronectin, laminin, poly-D-lysine, poly-L-ornithine, proteoglycan, vitronectin, polysaccharide, hydrogel, and combinations thereof.

11. The device of claim 1, wherein the agent is selected from the group consisting of polypeptide, entactin, glycoprotein, collagen, fibronectin, laminin, poly-D-lysine, poly-L-ornithine, proteoglycan, vitronectin, polysaccharide, hydrogel, and combinations thereof.

12. The device of claim 1, wherein the body, porous membrane, or both, comprise a material selected from the group consisting of polycarbonate, polyester, nylon, polyethersulfone, polypropylene, polytetrafluoroethylene, polyvinylidene difluoride, cellulose acetate, polydimethylsiloxane, inorganic ceramic and combinations thereof.

13. The device of claim 1, wherein at least one side of the porous membrane is seeded with a layer of a first cell type, and wherein the bottom compartment is seeded with a layer of a second cell type.

14. The device of claim 13, wherein the first and second cell types are selected from the group consisting of stem, epithelial, endothelial, smooth-muscle, neural, cardiac, and immune cells.

15. The device of claim 13, wherein the top side of the membrane is coated with airway-derived epithelial cells, and the bottom compartment is coated with airway-derived smooth-muscle cells.

16. The device of claim 13, wherein magnetic beads are attached to cells of the first, second, or both cell types.

17. The device of claim 16, wherein the magnetic beads are ferromagnetic or paramagnetic.

18. The device of claim 13, wherein magnetic beads are attached to cells in the bottom compartment.

19. The device of claim 18, wherein the magnetic beads are ferromagnetic, ferromagnetic or paramagnetic.

20. The device of claim 1, wherein one side of the porous membrane is seeded with a layer of a first cell type, and an opposing side of the porous membrane is seeded with a layer of a second cell type.

21. The device of claim 1, wherein a bottom side of the porous membrane is seeded with a layer of a first cell type, and wherein the bottom compartment is seeded with a layer of a second cell type.

22. The device of claim 1, wherein a top side of the porous membrane is seeded with a layer of a first cell type, and wherein the bottom compartment is seeded with a layer of a second cell type.

23. A method for performing a biological assay comprising:
providing a device of claim 1, wherein at least one side of the porous membrane and the bottom compartment are coated with living cells, the cells in the bottom compartment being attached to magnetic beads;
applying a magnetic field in a first direction to magnetize the magnetic beads attached to the cells; and
monitoring behavior of the cells in the bottom compartment by applying a magnetic field oscillating in a second direction that forces the magnetic beads into a twisting motion.

24. The method of claim 23, wherein the first direction is perpendicular to the second direction.

25. The method of claim 23, wherein the first direction is in a plane parallel to the top surface of the porous membrane and the second direction is perpendicular to the top surface of the porous membrane.

26. The method of claim 23, wherein the twisting motion comprises movement in the first direction and movement in the second direction.

27. The method of claim 26, further comprising recording the movement in the first direction.

28. The method of claim 26, further comprising recording the movement in the second direction.

29. The method of claim 27, wherein the recording comprises a microscope imaging the magnetic beads.

30. A method for determining an effect of at least one stimulus on cells within the device set forth in claim 1, the method comprising:
applying a stimulus to the top compartment, bottom compartment, or both; and
monitoring behavior of cells in the bottom compartment.

31. The method of claim 30, wherein the stimulus is physical, chemical, or biological in nature.

32. The method in claim 31, wherein the stimulus is physical.

33. The method of claim 32, wherein the physical stimulus is an application of pressure to the top compartment at a level between about 0 to 100 cm H2O to cause compressive stress on the cells attached to the membrane.

34. The method of claim 30, wherein monitoring comprises assaying secretion and biochemical activity profiles, microrheological characteristics, or mechanical properties of the cells.

35. The method of claim 30, wherein the stimulus is a biological molecule.

36. The method of claim 35, wherein the biological molecule is a ligand selected from the group consisting of drugs or drug candidates, natural compounds, toxins, smoke, allergens, molds, pollen, nanoparticles, mineral dust, nucleic acids, viruses, bacteria, microbes, cells, hormones, growth factors, and cytokines.

37. The method of claim 30, further comprising:
applying a magnetic field in a first direction to magnetize magnetic beads attached to the cells; and
monitoring behavior of the cells in the bottom compartment by applying a magnetic field oscillating in a second direction that forces the magnetic beads into a twisting motion.

38. The method of claim 37, wherein the first direction is perpendicular to the second direction.

39. The method of claim 37, wherein the first direction is in a plane parallel to the top surface of the porous membrane and the second direction is perpendicular to the top surface of the porous membrane.

40. The method of claim 37, wherein the twisting motion comprises movement in the first direction and movement in the second direction.

41. The method of claim 40, further comprising recording the movement in the first direction.

42. The method of claim 41, wherein the recording comprises a microscope imaging the magnetic beads.

43. The method of claim 40, further comprising recording the movement in the second direction.

\* \* \* \* \*